(12) United States Patent
Cao et al.

(10) Patent No.: US 9,603,894 B2
(45) Date of Patent: Mar. 28, 2017

(54) MATERIALS PRESENTING NOTCH SIGNALING MOLECULES TO CONTROL CELL BEHAVIOR

(75) Inventors: Lan Cao, Stoughton, MA (US); Kamal H. Bouhadir, Beirut (LB); David J. Mooney, Sudbury, MA (US)

(73) Assignee: President and Fellows of Harvard College, Cambridge, MS (US)

( * ) Notice: Subject to any disclaimer, the term of this patent is extended or adjusted under 35 U.S.C. 154(b) by 0 days.

(21) Appl. No.: 13/883,005

(22) PCT Filed: Nov. 8, 2011

(86) PCT No.: PCT/US2011/059710
§ 371 (c)(1),
(2), (4) Date: Aug. 21, 2013

(87) PCT Pub. No.: WO2012/064697
PCT Pub. Date: May 18, 2012

(65) Prior Publication Data
US 2013/0331343 A1    Dec. 12, 2013

Related U.S. Application Data

(60) Provisional application No. 61/411,129, filed on Nov. 8, 2010.

(51) Int. Cl.
| | | |
|---|---|---|
| *A61K 38/10* | (2006.01) | |
| *A61K 38/17* | (2006.01) | |
| *A61K 47/48* | (2006.01) | |

(52) U.S. Cl.
CPC .......... *A61K 38/10* (2013.01); *A61K 38/1709* (2013.01); *A61K 47/4823* (2013.01); *A61K 47/48246* (2013.01)

(58) Field of Classification Search
CPC .................................................. A61K 38/10
See application file for complete search history.

(56) References Cited

U.S. PATENT DOCUMENTS

| | | |
|---|---|---|
| 3,773,919 A | 11/1973 | Boswell et al. |
| 4,522,811 A | 6/1985 | Eppstein et al. |
| 4,946,778 A | 8/1990 | Ladner et al. |
| 5,073,627 A | 12/1991 | Curtis et al. |
| 5,091,513 A | 2/1992 | Huston et al. |
| 5,132,405 A | 7/1992 | Huston et al. |
| 5,885,829 A | 3/1999 | Mooney et al. |
| 5,888,987 A | 3/1999 | Haynes et al. |
| 6,129,716 A | 10/2000 | Steer |
| 6,193,970 B1 | 2/2001 | Pardoll et al. |
| 6,251,396 B1 | 6/2001 | Gaur et al. |
| 6,281,256 B1 | 8/2001 | Harris et al. |
| 6,334,968 B1 | 1/2002 | Shapiro et al. |
| 6,403,374 B1 | 6/2002 | Tsien et al. |
| 6,429,199 B1 | 8/2002 | Krieg et al. |
| 6,511,650 B1 | 1/2003 | Eiselt et al. |
| 6,541,022 B1 | 4/2003 | Murphy et al. |
| 6,642,363 B1 | 11/2003 | Mooney et al. |
| 6,685,963 B1 | 2/2004 | Taupin et al. |
| 6,748,954 B2 | 6/2004 | Lee et al. |
| 6,767,928 B1 | 7/2004 | Murphy et al. |
| 6,783,712 B2 | 8/2004 | Slivka et al. |
| 6,790,840 B1 | 9/2004 | Lee et al. |
| 6,797,738 B2 | 9/2004 | Harris et al. |
| 6,800,733 B2 | 10/2004 | Tsien et al. |
| 7,157,566 B2 | 1/2007 | Tsien et al. |
| 7,186,413 B2 | 3/2007 | Bouhadir et al. |
| 7,192,693 B2 | 3/2007 | Bryant et al. |
| 7,427,602 B1 | 9/2008 | Shea et al. |
| 7,575,759 B2 | 8/2009 | Murphy et al. |
| 7,790,699 B2 | 9/2010 | Melvik et al. |
| 8,067,237 B2 | 11/2011 | Mooney et al. |
| 8,188,058 B2 | 5/2012 | Hackam et al. |
| 8,273,373 B2 | 9/2012 | Alsberg et al. |
| 8,728,456 B2 | 5/2014 | Sands et al. |
| 8,932,583 B2 | 1/2015 | Mooney et al. |
| 2002/0131853 A1 | 9/2002 | Nagasawa |
| 2002/0150604 A1 | 10/2002 | Yi et al. |

(Continued)

FOREIGN PATENT DOCUMENTS

| | | |
|---|---|---|
| CN | 101655611 A | 2/2010 |
| EP | 0562862 A1 | 9/1993 |

(Continued)

OTHER PUBLICATIONS

Chen et al, Adipogenic differentiation of adipose tissue-derived human mesenchymal stem cells: effect of gastric bypass surgery, Surg Endosc (2012) 26:3449-3456.*

Ugarte et al, Notch signaling enhances osteogenic differentiation while inhibiting adipogenesis in primary human bone marrow stromal cells, Experimental Hematology 2009;37:867-875.*

Merriam-Webster Dictionary Transient, download online on Jul. 18, 2014 from URL: <www.merriam-webster.com/dictionary/transient>.*

Liu et al, Heterobifunctional Poly(Ethylene Glycol)—Tethered Bone Morphogenetic Protein-2—Stimulated Bone Marrow Mesenchymal Stromal Cell Differentiation and Osteogenesis (Tissue Engineering, vol. 13, No. 5, 2007).*

(Continued)

*Primary Examiner* — James H Alstrum Acevedo
*Assistant Examiner* — Sergio Coffa
(74) *Attorney, Agent, or Firm* — McCarter & English, LLP; Maria Laccotripe Zacharakis

(57) ABSTRACT

The invention provides a solution to the problem of delivering molecules in a physiologically relevant manner to direct cell fate. For example, a Notch ligand molecule is presented in a microenvironment that mimics the environment encountered in vivo. Accordingly, the invention features a cell delivery vehicle comprising a biocompatible hydrogel or polymer and a composition that binds to a Notch receptor and methods of directing cell fate, e.g., stem cell differentiation, using such compositions.

5 Claims, 1 Drawing Sheet

(56) References Cited

U.S. PATENT DOCUMENTS

| | | |
|---|---|---|
| 2003/0075822 A1 | 4/2003 | Slivka et al. |
| 2003/0082806 A1 | 5/2003 | Berenson et al. |
| 2003/0095994 A1 | 5/2003 | Geistlich et al. |
| 2003/0100527 A1 | 5/2003 | Krieg et al. |
| 2003/0232895 A1 | 12/2003 | Omidian et al. |
| 2004/0058883 A1 | 3/2004 | Phillips et al. |
| 2004/0063206 A1 | 4/2004 | Rowley et al. |
| 2004/0136968 A1 | 7/2004 | Zheng et al. |
| 2004/0151764 A1 | 8/2004 | Zamora |
| 2004/0220111 A1 | 11/2004 | Kleinman et al. |
| 2004/0242469 A1 | 12/2004 | Lee et al. |
| 2004/0242482 A1 | 12/2004 | Gehring et al. |
| 2005/0002915 A1 | 1/2005 | Atala et al. |
| 2005/0053667 A1 | 3/2005 | Irvine et al. |
| 2005/0079159 A1 | 4/2005 | Shastri et al. |
| 2005/0090008 A1 | 4/2005 | Segura et al. |
| 2005/0106211 A1 | 5/2005 | Nelson et al. |
| 2005/0154376 A1 | 7/2005 | Riviere et al. |
| 2005/0177249 A1 | 8/2005 | Kladakis et al. |
| 2006/0083712 A1 | 4/2006 | Anversa |
| 2006/0141018 A1 | 6/2006 | Cochrum et al. |
| 2006/0264380 A1 | 11/2006 | Hellstrom et al. |
| 2007/0003595 A1 | 1/2007 | Wang et al. |
| 2007/0020232 A1 | 1/2007 | Rossignol et al. |
| 2007/0026518 A1* | 2/2007 | Healy et al. ............... 435/325 |
| 2007/0081972 A1 | 4/2007 | Sandler et al. |
| 2007/0116680 A1 | 5/2007 | Stegemann et al. |
| 2007/0178159 A1 | 8/2007 | Chen et al. |
| 2007/0190646 A1 | 8/2007 | Engler et al. |
| 2008/0044900 A1 | 2/2008 | Mooney et al. |
| 2008/0044990 A1 | 2/2008 | Lee |
| 2008/0051490 A1 | 2/2008 | Williams et al. |
| 2008/0138416 A1 | 6/2008 | Rauh et al. |
| 2008/0206308 A1 | 8/2008 | Jabbari et al. |
| 2008/0268052 A1 | 10/2008 | Voytik-Harbin et al. |
| 2009/0017096 A1 | 1/2009 | Lowman et al. |
| 2009/0192079 A1 | 7/2009 | Santos et al. |
| 2009/0238853 A1 | 9/2009 | Liu et al. |
| 2009/0297579 A1 | 12/2009 | Semino et al. |
| 2009/0305983 A1 | 12/2009 | Ying et al. |
| 2010/0015709 A1 | 1/2010 | Rehfeldt et al. |
| 2010/0055186 A1 | 3/2010 | Dadsetan et al. |
| 2010/0080816 A1 | 4/2010 | Hadeiba et al. |
| 2010/0129422 A1 | 5/2010 | Han et al. |
| 2010/0159008 A1 | 6/2010 | Barron et al. |
| 2010/0189760 A1 | 7/2010 | Schaffer et al. |
| 2010/0190741 A1 | 7/2010 | Cohen et al. |
| 2010/0272771 A1 | 10/2010 | Harlow et al. |
| 2011/0020216 A1 | 1/2011 | Mooney et al. |
| 2011/0117170 A1 | 5/2011 | Cao et al. |
| 2012/0100182 A1 | 4/2012 | Mooney et al. |
| 2012/0121539 A1 | 5/2012 | Sands et al. |
| 2012/0122218 A1 | 5/2012 | Huebsch et al. |
| 2012/0134967 A1 | 5/2012 | Mooney et al. |
| 2012/0256336 A1 | 10/2012 | Yano et al. |
| 2012/0264599 A1 | 10/2012 | Komatsu et al. |
| 2012/0329791 A1 | 12/2012 | Ashwell et al. |
| 2013/0029030 A1 | 1/2013 | Larsen |
| 2013/0177536 A1 | 7/2013 | Mooney et al. |
| 2013/0202707 A1 | 8/2013 | Ali et al. |
| 2013/0302396 A1 | 11/2013 | Mooney et al. |
| 2014/0079752 A1 | 3/2014 | Huebsch et al. |
| 2014/0112990 A1 | 4/2014 | Bencherif et al. |
| 2014/0178964 A1 | 6/2014 | Mooney et al. |
| 2014/0193488 A1 | 7/2014 | Kim et al. |
| 2014/0227327 A1 | 8/2014 | Bencherif et al. |
| 2014/0234423 A1 | 8/2014 | Sands et al. |
| 2015/0024026 A1 | 1/2015 | Mooney et al. |

FOREIGN PATENT DOCUMENTS

| | | |
|---|---|---|
| EP | 1452191 A2 | 9/2004 |
| EP | 1561481 A2 | 8/2005 |
| JP | 2005170816 A | 6/2005 |
| WO | WO-9616086 A1 | 5/1996 |
| WO | WO-9812228 A1 | 3/1998 |
| WO | WO-9951259 A2 | 10/1999 |
| WO | WO-0135932 A2 | 5/2001 |
| WO | WO-0216557 A2 | 2/2002 |
| WO | WO-03020884 A2 | 3/2003 |
| WO | WO-2004006990 A2 | 1/2004 |
| WO | WO-2004030706 A2 | 4/2004 |
| WO | WO-2004089413 A1 | 10/2004 |
| WO | WO-2005026318 A2 | 3/2005 |
| WO | WO-2005037190 A2 | 4/2005 |
| WO | WO-2005037293 A1 | 4/2005 |
| WO | WO-2005046748 A1 | 5/2005 |
| WO | WO-2005072088 A2 | 8/2005 |
| WO | WO 2006/085879 * | 8/2006 |
| WO | WO-2006119619 A1 | 11/2006 |
| WO | WO-2006136905 A2 | 12/2006 |
| WO | WO-2007030901 A1 | 3/2007 |
| WO | WO-2007064152 A1 | 6/2007 |
| WO | WO-2007070660 A2 | 6/2007 |
| WO | WO-2007078196 A1 | 7/2007 |
| WO | WO-2007107739 A1 | 9/2007 |
| WO | WO-2007150020 A1 | 12/2007 |
| WO | WO-2008018707 A1 | 2/2008 |
| WO | WO-2009002401 A2 | 12/2008 |
| WO | WO-2009005769 A2 | 1/2009 |
| WO | WO-2009074341 A1 | 6/2009 |
| WO | WO-2009102465 A2 | 8/2009 |
| WO | WO-2009146456 A1 | 12/2009 |
| WO | WO-2009155583 A1 | 12/2009 |
| WO | WO-2010120749 A2 | 10/2010 |
| WO | WO-2011014871 A1 | 2/2011 |
| WO | WO-2011063336 A2 | 5/2011 |
| WO | WO-2011109834 A2 | 9/2011 |
| WO | WO-2011130753 A2 | 10/2011 |
| WO | WO-2011150240 A1 | 12/2011 |
| WO | WO-2011151431 A1 | 12/2011 |
| WO | WO-2011163669 A2 | 12/2011 |
| WO | WO-2012009611 A2 | 1/2012 |
| WO | WO-2012019049 A1 | 2/2012 |
| WO | WO-2012048165 A2 | 4/2012 |
| WO | WO-2012064697 A2 | 5/2012 |
| WO | WO-2012148684 A1 | 11/2012 |
| WO | WO-2012149358 A1 | 11/2012 |
| WO | WO-2012167230 A1 | 12/2012 |
| WO | WO-2013106852 A1 | 7/2013 |
| WO | WO-2013158673 A1 | 10/2013 |

OTHER PUBLICATIONS de Jong et al, Regulation of Notch signaling genes during BMP2-induced differentiation of osteoblast precursor cells (Biochemical and Biophysical Research Communications 320 (2004) 100-107).*

Miljkovic et al, Chondrogenesis, bone morphogenetic protein-4 and mesenchymal stem cells (Osteoarthritis and Cartilage (2008) 16, 1121e1130).*

BMP-4 BLAST, Mar. 4, 2015.*

Nobta et al (J Biol Chem. Apr. 22, 2005;280(16):15842-8).*

Alsberg et al. "Regulating Bone Formation via Controlled Scaffold Design." *J. Dent. Res.* 82.11(2003):903-908.

Augst et al. "Alginate Hydrogels as Biomaterials." *Macromol. Biosci.* 6(2006):623-633.

Bachem et al. "Superior Antigen Cross-Presentation and XCR1 Expression Define Human CD11c+CD141+ Cells as Homologues of Mouse CD8+ Dendritic Cells." *J. Exp. Med.* 207.6(2010):1273-1281.

Bouhadir et al. "Degradation of Partially Oxidized Alginate and its Potential Application for Tissue Engineering." *Biotechnol. Prog.* 17.5(2001):945-950.

Bryant et al. "Photo-Patterning of Porous Hydrogels for Tissue Engineering." *Biomater.* 28.19(2007):2978-2986.

Kong et al. "Controlling Degradation of Hydrogels via the Size of Crosslinked Junctions." *Adv. Mater.* 16.21(2004):1917-1921.

Kong et al. "Decoupling the Dependence of Rheological/Mechanical Properties of Hydrogels from Solids Concentration." *Polymer.* 43(2002):6239-6246.

Kong et al. "Design of Biodegradable Hydrogel for the Local and Sustained Delivery of Angiogenic Plasmid DNA." *Pharma. Res.* 25.5(2008):1230-1238.

(56) References Cited

OTHER PUBLICATIONS

Langenkamp et al. "Kinetics of Dendritic Cell Activation: Impact on Priming of TH1, TH2 and Nonpolarized T Cells." *Nat. Immunol.* 1.4(2000):311-316.

Lauterbach et al. "Mouse CD8α+ DCs and Human BDCA3+ DCs are Major Producers of IFN-λ in Response to Poly IC." *J. Exp. Med.* 207.12(2010):2703-2717.

Leor et al. "Cells, Scaffolds, and Molecules for Myocardial Tissue Engineering." *Pharmacol. Therapeutics.* 105(2005):151-163.

Lutolf et al. "Repair of Bone Defects Using Synthetic Mimetics of Collagenous Extracellular Matrices." *Nat. Biotechnol.* 21.5(2003):513-518.

Pedersen et al. "Induction of Regulatory Dendritic Cells by Desamethasone and 1α,25-Dihydroxyvitamin D3." *Immunol. Lett.* 91(2004):63-69.

Reis e Sousa. "Activation of Dendritic Cells: Translating Innate into Adaptive Immunity." *Curr. Opin. Immunol.* 16.1(3005):21-25.

Silva et al. "Material-Based Deployment Enhances Efficacy of Endothelial Progenitor Cells." *PNAS.* 105.38(2008):14347-14352.

"Wound Management: Past, Present, and Future." *Clinicians' Pocket Guide to Chronic Wound Repair.* Mulder et al., eds. Springhouse, PA: Springhouse Corporation. (1998):85-90.

Anderson et al. "Biomaterial Microarrays: Rapid, Microscale Screening of Polymer-Cell Interaction." *Biomaterials.* 26.23(2005):4892-4897.

Anderson et al. "Nanoliter-Scale Synthesis of Arrayed Biomaterials and Application to Human Embryonic Stem Cells." *Nat. Biotechnol.* 22.7(2004):863-866.

Balakrishna et al. "Structural Correlates of Antibacterial and Membrane-Permeabilizing Activities in Acylpolyamines." *Antimicrob. Agents Chemother.* 50.3(2006):852-861.

Bar-Cohen et al. "Electroactive Polymer Actuators and Sensors." *MRS Bullet.* 33.3(2008):173-181.

Bar-Or et al. "Induction of Antigen-Specific Tolerance in Multiple Sclerosis after Immunization with DNA Encoding Myelin Basic Protein in a Randomized, Placebo-Controlled Phase 1/2 Trial." *Arch. Neurol.* 64.10(2007):1407-1415.

Bates. "Improved Muscle Regeneration by Combining VEGF With IGF1." *Regen. Med.* 5.6(2010):853-854.

Beaucage et al. "The Functionalization of Oligonucleotides Via Phosphoramidite Derivatives." *Tetrahedron.* 49.10(1993):1925-1963.

Beebe et al. "Functional Hydrogel Structures for Autonomous Flow Control Inside Microfluidic Channels." *Nature.* 404(2000):588-590.

Bekiari et al. "Study of Poly(N,N-dimethylacrylamide)/CdS Nanocomposite Organic/Inorganic Gels." *Langmuir.* 20.19(2004):7972-7975.

Blumenthal et al. "Polyurethane Scaffolds Seeded with Genetically Engineered Skeletal Myoblasts: A Promising Tool to Regenerate Myocardial Function." *Artificial Organs.* 34.2(2010):E46-E54.

Brinkmann et al. "Neutrophil Extracellular Traps Kill Bacteria." *Science.* 303.5663(2004):1532-1535.

Calvert. "Electroactive Polymer Gels." *Electroactive Polymer (EAP) Acutators as Artificial Muscle: Reality, Potential, and Challenges.* Bar-Cohen, ed. Bellingham, WA: Spie Press. (2004):151-170.

Calvert. "Gel Sensors and Actuators." *MRS Bullet.* 33.3(2008):207-212.

Conconi et al. "In vitro and in vivo Evaluation of Acellular Diaphragmatic Matrices Seeded with Muscle Precursors Cells and Coated with VEGF Silica Gel to Repair Muscle Defect of the Diaphragm." *J. Biomed. Mater. Res.* 89A.2(2009):304-316.

Coulson et al. "Flow of Fluids through Granular Beds and Packed Columns." *Chemical Engineering.* New York: Pergamon Press. 2(1978):125-171.

Crameri et al. "Improved Green Fluorescent Protein by Molecular Evolution Using DNA Shuffling." *Nat. Biotechnol.* 14.3(1996):315-319.

De Temmerman et al. "Particulate Vaccines: On the Quest for Optimal Delivery and Immune Response." *Drug Disc. Today.* 16.13/14(2011):569-582.

Doan et al. "Subcellular Localization of a Sporulation Membrane Protein is Achieved Through a Network of Interactions Along and Across the Septum." *Mol. Microbiol.* 55.6(2005):1767-1781.

Egholm et al. "Peptide Nucleic Acids (PNA). Oligonucleotide Analogues with an Achiral Peptide Backbone." *J. Am. Chem. Soc.* 114.5(1992):1895-1897.

Egholm et al. "PNA Hybridizes to Complementary Oligonucleotides Obeying the Watson-Crick Hydrogen-Bonding Rules." *Nature.* 365.6446(1993):566-568.

Falsey et al. "Peptide and Small Molecule Microarray for High Throughput Cell Adhesion and Functional Assays." *Bioconjug. Chem.* 12.3(2001):346-353.

Fischer et al. "A Brilliant Monomeric Red Fluorescent Protein to Visualize Cytoskeleton Dynamics in Dictyostelium." *FEBS Lett.* 577.1-2(2004):227-232.

Fischer et al. "Visualizing Cytoskeleton Dynamics in Mammalian Cells Using a Humanized Variant of Monomeric Red Fluorescent Protein." *FEBS Lett.* 580.10(2006):2495-2502.

Fox. "Management of Worsening Multiple Sclerosis with Mitoxantrone: A Review." *Clin. Ther.* 28.4(2006):461-474.

GenBank Accession No. AAI44040, Mar. 18, 2009.
GenBank Accession No. CAG29322.1, Oct. 16, 2008.
GenBank Accession No. CAG33149.1, Oct. 21, 2008.
GenBank Accession No. EF064765.1, Nov. 13, 2006.

Glasbey et al. "Image Analysis and Three-Dimensional Modelling of Pores in Soil Aggregates." *Eur. J. Soil Sci.* 42.2(1991):479-486.

Gupta et al. "Magnetically Controlled Targeted Micro-Carrier Systems." *Life Sci.* 44.3(1989):175-186.

Hamdy et al. "Targeting Dendritic Cells with Nano-Particulate PLGA Cancer Vaccine Formulations." *Adv. Drug Deliv. Rev.* 63.10(2011):943-955.

Heath. "Cells for Tissue Engineering." *Trends Biotechnol.* 18.1(2006):17-19.

Iwamoto et al. "Preparation of an Ionic Polymer Gel Microactuator and Measurement of its Periodic Motions." *Nippon Kagaku Kaishi.* 9(1997):609-614. (Japanese Original and English Abstract).

Juntanon et al. "Electrically Controlled Release of Sulfosalicylic Acid from Crosslinked Poly(Vinyl Alcohol) Hydrogel." *Int. J. Pharm.* 356(2008):1-11.

Khownium et al. "Novel Endotoxin-Compounds with Terephthalaldehyde-bis-guanylhydrazone Scaffolds." *Bioorg. Med. Chem. Lett.* 16(2006):1305-1308.

Kim et al. "The Effect of VEGF on the Myogenic Differentiation of Adipose Tissue Derived Stem Cells Within Thermosensitive Hydrogel Matrices." *Biomaterials.* 31.6(2010):1213-1218.

Krishnamachari et al. "PLGA Microparticles that Co-Deliver Antigen and Toll Like Receptor Ligand Adjuvants for Applications in Cancer Immunotherapy." AAPS Pharmaceutica. Nov. 11, 2009. Web. Mar. 1, 2013. http://abstracts.aapspharmaceutica.com/ExpoAAPS09/CC/forms/attendee/index.aspx?content=sessionInfo&sessionId=2716.

Kwon et al. "Electrically Erodible Polymer Gel for Controlled Release of Drugs." *Nature.* 354(1991):291-293.

Lao et al. "Magnetic and Hydrogel Composite Materials for Hyperthermia Applications." *J. Mater. Sci. Mater. Med.* 15.10(2004):1061-1064.

Letsinger et al. "Phosphoramidate Analogs of Oligonucleotides." *J. Org. Chem.* 35.11(1970):3800-3803.

Liu et al. "Nanostructured Materials Designed for Cell Binding and Transduction." *Biomacromolecules.* 2.2(2001):362-368.

López et al. "Magnetic Applications of Polymer Gels." *Macromol. Symp.* 166.1(2001):173-178.

Meier et al. "Peptide Nucleic Acids (PNAs)—Unusual Properties of Noionic Oligonucleotide Analogues." *Angew. Chem. Int. Ed.* 31.8(1992):1008-1010.

Meraz et al. "Mesoporous Silicon Particles for the Presentation of Tumor Antigens and Adjuvant for Anti-Cancer Immunity." *Cancer Res.* 71.S24(2011):159s-160s. (Abstract #P1-01-12).

(56) References Cited

OTHER PUBLICATIONS

Miller et al. "Lipopolysaccharide Sequestrants: Structural Correlates of Activity and Toxicity in Novel Acylhomospermines." *J. Med. Chem.* 48(2005):2589-2599.
Miyata et al. "Biomolecule-Sensitive Hydrogels." *Adv. Drug Deliv. Rev.* 54.1(2002):79-98.
Murdan. "Electro-Responsive Drug Delivery from Hydrogels." *J. Control. Release.* 92(2003):1-17.
Nagai et al. "A Variant of Yellow Fluorescent Protein with Fast and Efficient Maturation for Cell-Biological Applications." *Nat. Biotechnol.* 20.1(2002):87-90.
NCBI Accession No. NM_004119, Apr. 14, 2013.
NCBI Accession No. NM_006274.2, Mar. 31, 2013.
Niamlang et al. "Electrically Controlled Release of Salicylic Acid from poly(p-phenylene vinylene) Polyacrylamide Hydrogels." *Int. J. Pharm.* 371(2009):126-133.
Orner et al. "Arrays for the Combinatorial Exploration of Cell Adhesion." *J. Am. Chem. Soc.* 126.35(2004):10808-10809.
Paradee et al. "Effects of Crosslinking Ratio, Model Drugs, and Electric Field Strength on Electrically Controlled Release for Alginate-Based Hydrogels." *J. Mater. Sci. Mater. Med.* 23(2012):999-1010.
Parker et al. "Effect of Mitoxantrone on Outcome of Children with First Relapse of Acute Lymphoblastic Leukemia (ALL R3): An Open-Label Radomised Trial." *Lancet.* 376(2010):2009-2017.
Porter et al. "Separation of Natural Populations of Coliform Bacteria from Freshwater and Sewage by Magnetic-Bead Cell Sorting." *J. Microbiol. Meth.* 33.3(1998):221-226.
Qui et al. "Environment-Sensitive Hydrogels for Drug Delivery." *Adv. Drug Deliv. Rev.* 53.3(2001):321-339.
Rhoads et al. "Satellite Cell-Mediated Angiogenesis in vitro Coincides with a Functional Hypoxia-Inducible Factor Pathway." *Am. J. Physiol. Cell Physiol.* 296.6(2009):C1321-C1328.
Rizzo et al. "An Improved Cyan Fluorescent Protein Variant Useful for FRET." *Nat. Biotechnol.* 22.4(2004):445-449.
Salvador et al. "Combination of Immune Stimulating Adjuvants With Poly(lactide-co-glycolide) Microspheres Enhances the Immune Response of Vaccines." *Vaccine.* 30.3(2011):589-596.
Salvay et al. "Inductive Tissue Engineering with Protein and DNA-Releasing Scaffolds." *Mol. Biosyst.* 2.1(2006):36-48.
Shakweh et al. "Design and Characterisation of Poly(lactide-co-glycolide) Small Particulate Systems for the Delivery of Immunostimulant CpG Oligonucleotide." *J. Nanosci. Nanotechnol.* 6.9-10(2006):2811-2820.
Shaner et al. "Improved Monomeric Red, Orange and Yellow Fluorescent Proteins Derived from *Discosoma* sp. Red Fluorescent Protein." *Nat. Biotechnol.* 22.12(2004):1567-1572.
Takahashi et al. "Induction of Pluripotent Stem Cells from Adult Human Fibroblasts by Defined Factors." *Cell.* 131.5(2007):861-872.
Tanaka et al. "Collapse of Gels in an Electric Field." *Science.* 218(1982):467-469.
ten Dijke et al. "Growth Factors for Wound Healing." *Nat. Biotechnol.* 7(1989):793-798.
Tomer et al. "Electrically Controlled Release of Macromolecules from Cross-Linked Hyaluronic Acid Hydrogels." *J. Control. Release.* 33.3(1995):405-413.
Tourniaire et al. "Polymer Microarrays for Cellular Adhesion." *Chem. Commun.* 20(2006):2118-2120.
Tsien. "The Green Fluorescent Protein." *Annu. Rev. Biochem.* 67(1998):509-544.
Wang et al. "Evolution of New Nonantibody Proteins via Iterative Somatic Hypermutation." *PNAS.* 101.48(2004):16745-16749.
Xie et al. "Preparation and Application of Surface-Coated Superparamagnetic Nanobeads in the Isolation of Genomic DNA." *J. Magn. Magnetic Mater.* 277.1(2004):16-23.
Yu et al. "Induced Pluripotent Stem Cell Lines Derived from Human Somatic Cells." *Science.* 318.5858(2007):1917-1920.
Yuk et al. "Electric Current-Sensitive Drug Delivery System Using Sodium Alginate/Polyacrylic Acid Composites." *Pharm. Res.* 9.7(1992):955-957.
Dar et al. "Optimization of Cardiac Cell Seeding and Distribution in 3D Porous Alginate Scaffolds." *Biotechnol. Bioeng.* 80(2002):305-312.
Marui et al. "Simultaneous Application of Basic Fibroblast Growth Factor and Hepatocyte Growth Factor to Enhance the Blood Vessels Formation." *J. Vasc. Surg.* 41.1(2005):82-90.
Mohan et al. "Novel Porous, Polysaccharide Scaffolds for Tissue Engineering Applications." *Trends Biomater. Artif. Organs.* 18.2(2005):219-224.
Ohashi et al. "Surgical Excision Combined with Autologous Whole Tumor Cell Vaccination is an Effective Therapy for Murine Neuroblastoma." *J. Ped. Surg.* 41(2006):1361-1368.
Salem et al. "Defining the Antigen-Specific T-Cell Response to Vaccination and Poly(I:C)/TLR3 Signaling." *J. Immunother.* 28.3(2005):220-228.
Sarkar et al. "Condensation of Oligonucleotides Assembled into Nicked and Gapped Duplexes: Potential Structures for Oligonucleotide Delivery." *Nucleic Acids Res.* 33.1(2005):143-151.
Shoichet et al. "Stability of Hydrogels Used in Cell Encapsulation: An In Vitro Comparison of Alginate and Agarose." *Biotechnol. Bioeng.* 50(1996):374-381.
"Antigens and Receptors." *Immunology.* Doan et al., eds. Philadelphia: Wolters Kluwer/Lippincott Williams & Wilsons. (2008):11-23.
Abrahams et al. "Expression and Secretion of Antiviral Factors by Trophoblast Cells Following Stimulation by the TLF-3 Agonist, Poly (I:C)." *Hum. Reprod.* 21.9(2006):2432-2439.
Agrawal et al. "Cutting Edge: Different Toll-Like Receptor Agonists Instruct Dendritic Cells to Induce Distinct Th Responses via Differential Modulation of Extracellular Signal-Regulated Kinase-Mitogen-Activated Protein Kinase and c-Fos." *J. Immunol.* 171. 10(2003):4984-4989.
Akira et al. "Pathogen Recognition and Innate Immunity." *Cell.* 124.4(2006):783-801.
Akira et al. "Toll-Like Receptors: Critical Proteins Linking Innate and Acquired Immunity." *Nat. Immunol.* 2.8(2001):675-680.
Aldhous. "Print Me a Heart and a Set of Arteries." *New Scientist.* 2547(2006):19.
Ali et al. "Controlled Local Delivery of GM-CSF From Polymer-Based Vaccines Enhances Anti-Tumor Immune Responses by Priming Host Dendritic Cells." *2007 AACR Annual Meeting.* 48(2007):652. (Abstract #2736).
Ali et al. "Converging Cell Therapy with Biomaterials." *Cell Transplantation from Laboratory to Clinic.* Burlington, MA: Elsevier, Inc. (2006):591-609.
Ali et al. "In Situ Regulation of DC Subsets and T Cells Mediates Tumor Regression in Mice." *Sci. Transl. Med.* 1.8(2009):8-19.
Ali et al. "Infection-Mimicking Materials to Program Dendritic Cells in situ." *Nat. Mater.* 8.2(2009):151-158.
Ali et al. "Sustained GM-CSF and PEI Condensed pDNA Presentation Increases the Level and Duration of Gene Expression in Dendritic Cells." *J. Control. Release.* 132.3(2008):273-278.
Allen et al. "Regulation of Satellite Cells During Skeletal Muscle Growth and Development." *Proc. Soc. Exp. Biol. Med.* 194. 2(1990):81-86.
Allen et al. "Regulation of Skeletal Muscle Satellite Cell Proliferation by Bovine Pituitary Fibroblast Growth Factor." *Exp. Cell Res.* 152.1(1984):154-160.
Almarza et al. "Evaluation of Three Growth Factors in Combination of Two for Temporomandibular Joint Disc Tissue Engineering." *Arch. Oral Biol.* 51.3(2006):215-221.
Alsberg et al. "Cell-Interactive Alginate Hydrogels for Bone Tissue Engineering." *J. Dent. Res.* 80.11(2001):2025-2029.
Alsberg et al. "Engineering Growing Tissues." *PNAS.* 99.18(2002):12025-12030.
Anderson et al. "The NOD Mouse: A Model of Immune Dysregulation." *Annu. Rev. Immunol.* 23(2005):447-485.
Anderson. "A Role for Nitric Oxide in Muscle Repair: Nitric Oxide-Mediated Activation of Muscle Satellite Cells." *Mol. Biol. Cell.* 11(2000):1859-1874.

(56) References Cited

OTHER PUBLICATIONS

Arany et al. "At the Edge of Translation—Materials to Program Cells for Directed Differentiation." *Oral Dis.* 17.3(2011):241-251.
Atala et al. "Endoscopic Treatment of Vesicoureteral Reflux with a Chondrocyte-Alginate Suspension." *J. Urol.* 152(1994):641-643.
Bachelder et al. "Acid-Degradable Polyurethane Particles for Protein-Based Vaccines: Biological Evaluation and in Vitro Analysis of Particle Degradation Products." *Mol. Pharm.* 5.5(2008):876-884.
Badovinac et al. "Regulation of CD8 T+ Cells Undergoing Primary and Secondary Responses to Infection in the Same Host." *J. Immunol.* 170(2003):4933-4942.
Bakri et al. "Pharmacokinetics of Intravitreal Bevacizumab (Avastin)." *Ophthalmology.* 114.5(2007):855-859.
Banchereau et al. "Dendritic Cells and the Control of Immunity." *Nature.* 392.6673(1998):245-252.
Barbero et al. "Growth Factor Supplemented Matrigel Improves Ectopic Skeletal Muscle Formation—A Cell Therapy Approach." *J. Cell. Physiol.* 186(2001):186-192.
Barrio et al. "A Two-Dimensional Numerical Study of Spatial Pattern Formation in Interacting Turing Systems." *Bull. Math Biol.* 61.3(1999):483-505.
Beauchamp et al. "Dynamics of Myoblast Transplantation Reveal a Discrete Minority of Precursors with Stem Cell-Like Properties as the Myogenic Source." *J. Cell Biol.* 144.6(1999):1113-1122.
Bischoff. "Proliferation of Muscle Satellite Cells on Intact Myofibers in Culture." *Dev. Biol.* 115.1(1986):129-139.
Blanas et al. "Induction of Autoimmune Diabetes by Oral Administration of Autoantigen." *Science.* 274.5293(1996):1707-1709.
Bohl et al. "Role of Synthetic Extracellular Matrix in Development of Engineered Dental Pulp." *J. Biomater. Sci. Polym. Ed.* 9.7(1998):749-764.
Bonauer et al. "MicroRNA-92a Controls Angiogenesis and Functional Recovery of Ischemic Tissues in Mice." *Science.* 324.5935(2009):1710-1713.
Boontheekul et al. "Regulating Myoblast Phenotype Through Controlled Gel Stiffness and Degradation." *Tissue Engin.* 13.7(2007):1431-1442.
Borselli et al. "Functional Muscle Regeneration with Combined Delivery of Angiogenesis and Myogenesis Factors." *PNAS.* 107.8(2010):3287-3292.
Bouhadir et al. "Synthesis of Cross-Linked Poly(aldehyde guluronate) Hydrogels." *Polymer.* 40(1999):3575-3584.
Bowne et al. "Injection of DNA Encoding Granulocyte-Macrophage Colony-Stimulating Factor Recruits Dendritic Cells for Immune Adjuvant Effects." *Cytokines Cell Mol. Ther.* 5.4(1999):217-225.
Brinkman et al. "Photo-Cross Linking of Type 1 Collagen Gels in the Presence of Smooth Muscle Cells: Mechanical Properties, Cell Viability, and Function." *Biomacromolecules.* 4.4(2003):890-895.
Brouwers et al. "Can the Growth Factors PTHrP, Ihh and VEGF, Together Regulate the Development of a Long Bone?" *J. Biomech.* 39.15(2006):2774-2782.
Burdick et al. "Stimulation of Neurite Outgrowth by Neurotrophins Delivered From Degradable Hydrogels." *Biomater.* 27.3(2006):452-459.
Cao et al. "Promoting Angiogenesis via Manipulation of VEGF Responsiveness with Notch Signaling." *Biomater.* 30.25(2009):4085-4093.
Carlson et al. "Notch Signaling Pathway and Tissue Engineering." *Front. Biosci.* 12(2007):5143-5156.
Carmeliet et al. "Angiogenesis in Cancer and Other Diseases." *Nature.* 407.6801(2009):249-257.
Carmeliet. "Mechanisms of Angiogenesis and Arteriogenesis." *Nat. Med.* 6.4(2000):389-395.
Chan et al. "Antifibrotic Effects of Suramin in Injured Skeletal Muscle After Laceration." *J. Appl. Physiol.* 95(2003):771-780.
Chan et al. "Helix Induction in Antimicrobial Peptides by Alginate in Biofilms." *J. Biol. Chem.* 279.37(2004):38749-38754.
Chen et al. "Integrated Approach to a Designing Growth Factor Delivery Systems." *FASEB J.* 21.14(2007):3896-3903.

Chen et al. "Polymeric Growth Factor Delivery Strategies for Tissue Engineering." *Pharma. Res.* 20.8(2003):1103-1112.
Chen et al. "Skeletal Muscle Stem Cells." *Reprod. Biol. Endocrinol.* 1(2003):101.
Chen et al. "Spatio-Temporal VEGF and PDGF Delivery Patterns Blood Vessel Formation and Maturation." *Pharm. Res.* 24.2(2007):258-264.
Choi. "Replacement Organs, Hot Off the Press." *New Scientist.* 177.2379(2003):16.
Chromiak et al. "Bioreactor Perfusion System for the Long-Term Maintenance of Tissue-Engineered Skeletal Muscle Organoids." *In Vitro Cell Dev. Biol. Anim.* 34.9(1998):694-703.
Clauss et al. "Interstitial Transport of Rabbit and Sheep Antibodies in Normal and Neoplastic Tissues." *Cancer Res.* 50.12(1990):3487-3492.
Cohen et al. "Controlled Delivery Systems for Proteins Based on Poly(Lactic/Glycolic Acid) Microspheres." *Pharm. Res.* 8.6(1991):713-720.
Conboy et al. "The Regulation of Notch Signaling Controls Satellite Cell Activation and Cell Fate Determination in Postnatal Myogenesis." *Dev. Cell.* 3.3(2002):397-409.
Conn et al. "Purification of a Glycoprotein Vascular Endothelial Cell Mitogen from a Rat Glioma-Derived Cell Line." *PNAS.* 87.4(1990):1323-1327.
Cooper et al. "Extended Amplification In Vitro and Replicative Senescence: Key Factors Implicated in the Success of Human Myoblast Transplantation." *Hum. Gene Ther.* 14(2003):1169-1179.
Cornelison et al. "Single-Cell Analysis of Regulatory Gene Expression in Quiescent and Activated Mouse Skeletal Muscle Satellite Cells." *Dev. Biol.* 191.2(1997):270-283.
Cornelison et al. "Syndecan-3 and Syndecan-4 Specifically Mark Skeletal Muscle Satellite Cells and Are Implicated in Satellite Cell Maintenance and Muscle Regeneration." *Dev. Biol.* 239.1(2001):79-94.
Cullen et al. "Investigation of Vascular Endothelial Growth Factor Effects on Pulmonary Endothelial Monolayer Permeability and Neutrophil Transmigration." *Gen. Pharmacol.* 35.3(2000):149-157.
Curiel et al. "Tumor Immunotherapy: Inching Toward the Finish Line." *J. Clin. Invest.* 109.3(2002):311-312.
D'Amico et al. "The Early Progenitors of Mouse Dendritic Cells and Plasmacytoid Predendritic Cells are within the Bone Marrow Hemopoietic Precursors Expressing Flt3." *J. Exp. Med.* 198.2(2003):293-303.
Daro et al. "Polyethylene Glycomodified GM-CSF Expands CD11bhighCD11chigh but not CD11blowCD11chigh Murine Dendritic Cells In Vivo: A Comparative Analysis with Flt3 Ligand." *J. Immunol.* 165.1(2000):49-58.
den Haan et al. "CD8+ by not CD8– Dendritic Cells Cross-Prime Cytotoxic T Cells In Vivo." *J. Exp. Med.* 192.12(2000):1685-1696.
Dennis et al. "Excitability and Contractility of Skeletal Muscle Engineered From Primary Cultures and Cell Lines." *Am. J. Physiol. Cell Physiol.* 280(2001):C288-C295.
Dennis et al. "Excitability and Isometric Contractile Properties of Mammalian Skeletal Muscle Constructs Engineered in vitro." *In Vitro Cell Dev. Biol. Anim.* 36.5(2000):327-335.
Dieu et al. "Selective Recruitment of Immature and Mature Dendritic Cells by Distinct Chemokines Expressed in Different Anatomic Sites." *J. Exp. Med.* 188.2(1988):373-386.
Dor et al. "Making Vascular Networks in the Adult: Branching Morphogenesis Without a Roadmap." *Trends Cell Biol.* 13.3(2003):131-136.
Dranoff et al. "Vaccination with Irradiated Tumor Cells Engineered to Secrete Murine Granulocyte-Macrophage Colony-Stimulating Factor Stimulates Potent, Specific and Long-Lasting Anti-Tumor Immunity." *PNAS.* 90.8(1993):3539-3543.
Dranoff. "Cyotkines in Cancer Pathogenesis and Cancer Therapy." *Nat. Rev. Cancer.* 4.1(2004):11-22.
Dudley et al. "Adoptive Cell Transfer Therapy Following Non-Myeloablative by Lymphodepleting Chemotherapy for the Treatment of Patients with Refractory Metastatic Melanoma." *J. Clin. Oncol.* 23.10(2005):2346-2357.

(56) References Cited

OTHER PUBLICATIONS

Ehrbar et al. "Endothelial Cell Proliferation and Progenitor Maturation by Fibrin-Bound VEGF Variants with Differential Susceptibilities to Local Cellular Activity." *J. Control. Release.* 101(2004):93-109.
Eiselt et al. "Porous Carriers for Biomedical Applications Based on Alginate Hydrogels." *Biomat.* 21.19(2000):1921-1927.
El-Backly et al. "Regeneration of Dentine/Pulp-Like Tissue Using a Dental Pulp Stem Cell/Poly(lactic-co-glycolic) Acid Scaffold Construct in New Zealand White Rabbits." *Aust. Endod. J.* 34.2(2008):52-67.
Eldar et al. "Elucidating Mechanisms Underlying Robustness of Morphogen Gradients." *Curr. Opin. Genet. Dev.* 14.4(2004):435-439.
Eldar et al. "Robustness of the BMP Morphogen Gradient in *Drosophila* Embryonic Patterning." *Nature.* 419.6904(2002):304-308.
Eldar et al. "Self-Enhanced Ligand Degradation Underlies Robustness of Morphogen Gradients." *Dev. Cell.* 5.4(2003):635-646.
Engler et al. "Matrix Elasticity Directs Stem Cell Lineage Specification." *Cell.* 126.4(2006):677-689.
Ennett et al. "Temporally Regulated Delivery of VEGF in vitro and in vivo." *J. Biomed. Mater. Res. A.* 79.1(2006):176-184.
Faissner et al. "Boundaries and Inhibitory Molecules in Developing Neural Tissues." *Glia.* 13.4(1995):233-254.
Farrar et al. "T Helper Subset Development: Roles of Instruction, Selection, and Transcription." *J. Clin. Invest.* 109.4(2002):431-435.
Ferrara et al. "Angiogenesis as a Therapeutic Target." *Nature.* 438.7070(2005):967-974.
Ferrara et al. "Discovery and Development of Bevacizumab, an Anti-VEGF Antibody for Treating Cancer." *Nat. Rev. Drug Discov.* 3.5(2004):391-400.
Folkman. "Angiogenesis." *Annu. Rev. Med.* 57(2006):1-18.
Fonseca et al. "Capitalizing on the Immunogenicity of Dying Tumor Cells." *Clin. Cancer Res.* 14.16(2008):1603-1608.
Fontaine et al. "Surgical Treatment of Peripheral Circulation Disorders." *Helv. Chir. Acta.* 21.56(1954):499-533. (German Original, No English Translation Available).
Friedrich et al. "Promoter Traps in Embryonic Stem Cells: A Genetic Screen to Identify and Mutate Developmental Genes in Mice." *Genes Dev.* 5(1991):1513-1523.
Fukushima et al. "The Use of an Antifibrosis Agent to Improve Muscle Recovery After Laceration." *Am. J. Sports Med.* 29.4(2001):394-402.
Gamvrellis et al. "Vaccines that Facilitate Antigen Entry into Dendritic Cells." *Immunol. Cell Biol.* 82(2004):506-516.
GenBank Accession No. A32848.1, Jul. 5, 2002.
GenBank Accession No. AAA35789.1, Apr. 27, 1993.
GenBank Accession No. AAA56738.1, Dec. 7, 1994.
GenBank Accession No. AAA60552.1, Nov. 24, 2003.
GenBank Accession No. AAA64297.1, Mar. 24, 1995.
GenBank Accession No. AAB21432.2, Jun. 5, 2000.
GenBank Accession No. AAB29057.2, Mar. 6, 2001.
GenBank Accession No. AAB31818.1, Jan. 25, 1995.
GenBank Accession No. AAC16450.1, May 15, 1998.
GenBank Accession No. AAH07789.1, Jun. 9, 2008.
GenBank Accession No. AAH20698.1, Jul. 15, 2006.
GenBank Accession No. AAH32517.2, Jun. 9, 2008.
GenBank Accession No. AAH93731.1, Jul. 17, 2006.
GenBank Accession No. ABC86910, Jan. 3, 2011.
GenBank Accession No. CAA01954.1, Jun. 15, 1995.
GenBank Accession No. CAA40093.1, Oct. 7, 2008.
GenBank Accession No. CAA62632.1, Sep. 15, 1995.
GenBank Accession No. CAG46721.1, Jun. 29, 2004.
GenBank Accession No. CBI71013.1, Feb. 2, 2010.
GenBank Accession No. EU826563.1, Jul. 23, 2008.
GenBank Accession No. NM_000230.2, Dec. 17, 2012.
GenBank Accession No. NM_000514.3, Aug. 19, 2012.
GenBank Accession No. NM_000601.4, Nov. 25, 2012.
GenBank Accession No. NM_000614.3, Sep. 9, 2012.
GenBank Accession No. NM_000660.4, Dec. 9, 2012.
GenBank Accession No. NM_000800.3, Mar. 4, 2012.
GenBank Accession No. NM_001102654.1, Dec. 16, 2012.
GenBank Accession No. NM_001111283.1, Dec. 9, 2012.
GenBank Accession No. NM_001171630.1, Dec. 9, 2012.
GenBank Accession No. NM_001202.3, Nov. 18, 2012.
GenBank Accession No. NM_002506.2, Dec. 9, 2012.
GenBank Accession No. NM_002632.4, May 4, 2011.
GenBank Accession No. NM_003236.2, Aug. 21, 2011.
GenBank Accession No. NM_003263.3, Jan. 5, 2013.
GenBank Accession No. NM_003264.3, Jan. 6, 2013.
GenBank Accession No. NM_003268.5, Nov. 25, 2012.
GenBank Accession No. NM_006068.4, Oct. 28, 2012.
GenBank Accession No. NM_016562.3, Jan. 6, 2013.
GenBank Accession No. NM_030956.3, Oct. 28, 2012.
GenBank Accession No. NM_033023.4, Nov. 18, 2012.
GenBank Accession No. NM_138554.4, Dec. 29, 2012.
GenBank Accession No. NM_138636.4, Dec. 23, 2012.
GenBank Accession No. NM_170731.4, Dec. 9, 2012.
GenBank Accession No. NM_205819.3, Dec. 6, 2012.
GenBank Accession No. NM_205820.1, Jan. 5, 2013.
GenBank Accession No. NM_205823.2, Jan. 6, 2013.
GenBank Accession No. NP_001096124.1, Dec. 16, 2012.
GenBank Accession No. NP_002010.2, Dec. 9, 2012.
GenBank Accession No. NP_003254.2, Jan. 5, 2013.
GenBank Accession No. NP_003255.2, Jan. 6, 2013.
GenBank Accession No. NP_003259.2, Nov. 25, 2012.
GenBank Accession No. NP_006059.2, Oct. 28, 2012.
GenBank Accession No. NP_057646.1, Jan. 6, 2013.
GenBank Accession No. NP_112218.2, Oct. 28, 2012.
GenBank Accession No. NP_570912.2, Nov. 18, 2012.
GenBank Accession No. NP_612564.1, Dec. 29, 2012.
GenBank Accession No. NP_619542.1, Dec. 23, 2012.
GenBank Accession No. NP_991388.2, Dec. 6, 2012.
GenBank Accession No. NP_991389.1, Jan. 5, 2013.
GenBank Accession No. NP_991392.1, Jan. 6, 2013.
GenBank Accession No. P49771.1, Jan. 9, 2013.
Gerhardt et al. "VEGF Guides Angiogenic Sprouting Utilizing Endothelial Tip Cell Filopodia." *J. Cell Biol.* 161.6(2003):1163-1177.
Gilboa. "Dendritic-Cell Based Cancer Vaccines." *J. Clin. Invest.* 117.5(2007):1195-1203.
Gnjatic et al. "Toll-Like Receptor Agonists: Are They Good Adjuvants?" *Cancer J.* 16.4(2010):382-391.
Godbey et al. "Size Matters: Molecular Weight Affects the Efficiency of Poly(ethylenimine) as a Gene Delivery Vehicle." *J. Biomed. Mater. Res.* 45.3(1999):268-275.
Godbey et al. "Tracking the Intracellular Path of Poly(ethylenimine)/DNA Complexes for Gene Delivery." *PNAS.* 96.9(1999):5177-5181.
Gospodarowicz et al. "Effect of Fibroblast Growth Factor on the Division and Fusion of Bovine Myoblasts." *J. Cell Biol.* 70.2(1976):395-405.
Griffith et al. "Tissue Engineering—Current Challenges and Expanding Opportunities." *Science.* 295(2002):1009-1014.
Grimmer et al. "Tracheal Reconstruction Using Tissue-Engineered Cartilage." *Arch. Otolaryngol. Head Neck Surg.* 130.10(2004):1191-1196.
Gros et al. "A Common Somitic Origin for Embryonic Muscle Progenitors and Satellite Cells." *Nature.* 435(2005):954-958.
Gullberg et al. "Extracellular Matrix and Its Receptors During Development." *Int. J. Dev. Biol.* 39(1995):845-854.
Gussoni et al. "Dystrophin Expression and in the mdx Mouse Restored by Stem Cell Transplantation." *Nature.* 401(1999):390-394.
Hamby et al. "Small Molecule Inhibitors of Tumor-Promoted Angiogenesis, Including Protein Tyrosine Kinase Inhibitors." *Pharmacol. Ther.* 82.2-3(1999):169-193.
Hamilton et al. "GM-CSF Biology." *Growth Factors.* 22.4(2004):225-231.
Hamilton. "GM-CSF in Inflammation and Autoimmunity." *Trends Immunol.* 23.8(2002):403-408.

(56) References Cited

OTHER PUBLICATIONS

Hanada. "Efficacy of Rehabilitative Therapy in Regional Musculoskeletal Conditions." *Best Pract. Res. Clin. Rheumatol.* 17.1(2003):151-166.
Hansen et al. "Comparison of Clinical Grade Type 1 Polarized and Standard Matured Dendritic Cells for Cancer Immunotherapy." *Vaccine.* 31.4(2013):639-646.
Hansen et al. "Integrin Binding and Cell Spreading on Extracellular Matrix Act at Different Points in the Cell Cycle to Promote Hepatocyte Growth." *Mol. Biol. Cell.* 5(1994):967-975.
Harris et al. "Open Pore Biodegradable Matrices Formed with Gas Foaming." *J. Biomed. Mater. Res.* 42.3(1998):396-402.
Harrison. "What is the Status of Reaction-Diffusion Theory Thirty-Four Years After Turing?" *J. Theor. Biol.* 125.4(1987):369-384.
Hartgerink et al. "Peptide-Amphiphile Nanofibers: A Versatile Scaffold for the Preparation of Self-Assembling Materials." *PNAS.* 99.8(2002):5133-5138.
Hartmann et al. "CpG DNA: A Potent Signal for Growth, Activation, and Maturation of Human Dendritic Cells." *PNAS.* 96(1999):9305-9310.
Hashimoto et al. "Development of Alginate Wound Dressings Linked with Hybrid Peptides Derived from Laminin and Elastin." *Biomaterials.* 25.7-8(2004):1407-1414.
Hawke et al. "Myogenic Satellite Cells: Physiology to Molecular Biology." *J. Appl. Physiol.* 91(2001):534-551.
Helm et al. "Synergy Between Interstitial Flow and VEGF Directs Capillary Morphogenesis in vitro Through a Gradient Amplification Mechanism." *PNAS.* 102.44(2005):15779-15784.
Henry et al. "The VIVA Trial: Vascular Endothelial Growth Factor in Ischemia for Vascular Angiogenesis." *Circulation.* 107.10(2003):1359-1365.
Hermanson. *Bioconjugate Techniques.* New York: Academic Press. (1996):152-185.
Heslop et al. "Transplanted Primary Neonatal Myoblasts Can Give Rise to Functional Satellite Cells as Identified Using the Myf5nlacZI+ Mouse." *Gene Ther.* 8(2001):778-783.
Hildner et al. "Batf3 Deficiency Reveals a Critical Role for CD8α+ Dendritic Cells in Cytotoxic T Cell Immunity." *Science.* 322.5904(2008):1097-1100.
Hill et al. "Designing Scaffolds to Enhance Transplanted Myoblast Survival and Migration." *Tissue Engin.* 12.5(2006):1295-1304.
Hill et al. "Muscle Satellite (Stem) Cell Activation During Local Tissue Injury and Repair." *J. Anat.* 203.1(2003):89-99.
Hill. "Macroporous Scaffold Architecture, Peptide, HGF/FGF and Myoblast Incorporation Enhance Myogenesis." *IADR/AADR/CADR 83rd General Session.* (Mar. 9-12, 2005). Poster #2829.
Hirano et al. "Peptide and Protein Presenting Materials for Tissue Engineering." *Adv. Mat.* 16.1(2004):17-25.
Hodge-Dufour et al. "Inhibition of Interferon γ Induced Interleukin 12 Production: A Potential Mechanism for the Anti-Inflammatory Activities of Tumor Necrosis Factor." *PNAS.* 95.23(1998):13806-13811.
Hodi et al. "Immunologic and Clinical Effects of Antibody Blockade of Cytotoxic T Lymphocyte-Associated Antigen 4 in Previously Vaccinated Cancer Patients." *PNAS.* 105.8(2008):3005-3010.
Horsley et al. "IL-4 Acts as a Myoblast Recruitment Factor During Mammalian Muscle Growth." *Cell.* 113.4(2003):483-494.
Hsiong et al. "Differentiation Stage Alters Matrix Control of Stem Cells." *J. Biomed. Mater. Res. Part A.* 8(2007):145-456.
Huang et al. "Fabrication and in vitro Testing of Polymeric Delivery Systems for Condensed DNA." *J. Biomed. Mater. Res.* 67(2003):1384-1392.
Huang et al. "Long-Term In Vivo Gene Expression via Delivery of PEI-DNA Condensates From Porous Polymer Scaffolds." *Hum. Gene Ther.* 16.5(2005):609-617.
Hubbell et al. "Materials Engineering for Immunomodulation." *Nature.* 462(2009):449-460.
Hubbell. "Biomaterials in Tissue Engineering." *Bio/Tech.* 13(1995):565-576.
Huebsch et al. "Harnessing Traction-Mediated Manipulation of the Cell/Matrix Interface to Control Stem-Cell Fate." *Nat. Mater.* 9.6(2010):518-526.
Ishihara et al. "Roles of Bradykinin in Vascular Permeability and Angiogenesis in Solid Tumor." *Int. Immunopharmacol.* 2.4(2002):499-509.
Jain. "Molecular Regeneration of Vessel Maturation." *Nat. Med.* 9.6(2003):685-693.
Jain. "The Manufacturing Techniques of Various Drug Loaded Biodegradable Poly(lactide-co-glycolide) (PLGA) Devices." *Biomater.* 21.23(2000):2475-2490.
Jankovic et al. "In the Absence of IL-12, CD4+ T Cell Responses to Intracellular Pathogens Fail to Default to a Th2 Pattern and are Host Protective in an IL-10-/- Setting." *Immunity.* 16.3(2002):429-439.
Jego et al. "Plasmacytoid Dendritic Cells Induce Plasma Cell Differenetiation Through Type I Interferon and Interleukin 6." *Immunity.* 19.2(2003):225-234.
Jiang et al. "Self-Organization of Periodic Patterns by Dissociated Feather Mesenchymal Cells and the Regulation of Size, Number and Spacing of Primorida." *Development.* 126.22(1999):4997-5009.
Jinushi et al. "Enhancing the Clinical Activity of Granulocyte-Macrophage Colony-Stimulating Factor-Secreting Tumor Cell Vaccines." *Immunol. Rev.* 222(2008):287-298.
Jinushi et al. "MFG-E8-Mediated Uptake of Apoptotic Cells by APCs Links the Pro- and Antiinflammatory Activities of GM-CSF." *J. Clin. Invest.* 117.7(2007):1902-1913.
Johnson et al. "Activation of Skeletal Muscle Satellite Cells and the Role of Fibroblast Growth Factor Receptors." *Exp. Cell Res.* 219.2(1995):449-453.
Kanzler et al. "Therapeutic Targeting of Innate Immunity with Toll-Like Receptor Agaonists and Antagonists." *Nat. Med.* 13.5(2007):552-559.
Kawai et al. "Innate Immune Recognition of Viral Infection." *Nat. Immunol.* 7.2(2006):131-137.
Kawashima et al. "Pulmonary Delivery of Insulin With Nebulized DL-Lactide/Glycolide Copolymer (PLGA) Nanospheres to Prolong Hypoglycemic Effect." *J. Control. Release.* 62.1-2(1999):279-287.
Kim et al. "An Overview of Cartilage Tissue Engineering." *Yonsei Med. J.* 41.6(2000):766-773.
Kinoshita et al. "Successive Injections in MDX Mice of Myoblasts Grown with bFGF." *Neuromusc. Disord.* 6.3(1996):187-193.
Kisak et al. "The Vesosome—A Multicompartment Drug Delivery Vehicle." *Curr. Med. Chem.* 11.2(2004):199-219.
Klebanoff et al. "CD8+ T-Cell Memory in Tumor Immunology and Immunotherapy." *Immunol. Rev.* 211(2006):214-224.
Klinman. "Immunotherapeutic Uses of CpG Oligodeoxynucleotides." *Nat. Rev. Immunol.* 4.4(2004):249-258.
Kondo et al. "A Reaction-Diffusion Wave on the Skin of the Marine Angelfish *Pomacanthus.*" *Nature.* 376(2002):765-768.
Kong et al. "Controlling Rigidity and Degradation of Alginate Hydrogels via Molecular Weight Distribution." *Biomacromolec.* 5.5(2004):1720-1727.
Kong et al. "Designing Alginate Hydrogels to Maintain Viability of Immobilized Cells." *Biomat.* 24.22(2003):4023-4029.
Kong et al. "Non-Viral Gene Delivery Regulated by Stiffness of Cell Adhesion Substrates." *Nat. Mater.* 4(2005):406-410.
Krieg. "Development of TLR9 Agonists for Cancer Therapy." *J. Clin. Invest.* 117.5(2007):1184-1194.
Kumamoto et al. "Induction of Tumor-Specific Protective Immunity by in situ Langerhans Cell Vaccine." *Nat. Biotech.* 20(2002):64-69.
Kumar et al. "Toll-Like Receptors and Innate Immunity." *Biochem. Biophys. Res. Commun.* 388.4(2009):621-625.
Kurts et al. "CD8 T Cell Ignorance or Tolerance to Islet Antigens Depends on Antigen Dose." *PNAS.* 96.22(1999):12703-12707.
Kwon et al. "In vivo Targeting Dendritic Cells for Activation of Cellular Immunity Using Vaccine Carriers Based on pH-Responsive Microparticles." *PNAS.* 102.51(2005):18264-18268.
Langer et al. "Tissue Engineering." *Science.* 260(1993):920-926.
Lanzavecchia et al. "Regulation of T Cell Immunity by Dendritic Cells." *Cell.* 106.3(2001):263-266.

(56) References Cited

OTHER PUBLICATIONS

Leach et al. "Coating of VEGF-Releasing Scaffolds with Bioactive Glass for Angiogenesis and Bone Regeneration." *Biomater.* 27.17(2006):3249-3255.
Lee et al. "Hydrogel Formation via Vell Crosslinking." *Adv. Mat.* 15.21(2003):1828-1832.
Lee et al. "Hydrogels for Tissue Engineering." *Chem. Rev.* 101.7(2001):1869-1879.
Lefaucheur et al. "The Cellular Events of Injured Muscle Regeneration Depend on the Nature of the Injury." *Neuromusc. Disorders.* 5.6(1995):501-509.
Lensch et al. "Scientific and Clinical Opportunities for Modeling Blood Disorders With Embyronic Stem Cells." *Blood.* 107.7(2006):2605-2612.
Leshem et al. "Hepatocyte Growth Factor (HGF) Inhibits Skeletal Muscle Cell Differentiation: A Role for the bHLH Protein Twist and the cdk Inhibitor p27." *J. Cell. Physiol.* 184(2000):101-109.
Li et al. "Effect of Growth Factors and Extracellular Matrix Materials on the Proliferation and Differentiation of Microencapsulated Myoblasts." *J. Biomater. Sci. Polym. Ed.* 14.6(2003):533-549.
Li et al. "Effects of Three-Dimensional Scaffolds on Cell Organization and Tissue Development." *Biotech. Bioprocess Eng.* 6.5(2001):311-325.
Li. "TNF-$\alpha$ is a Mitogen is Skeletal Muscle." *Am. J. Physiol. Cell Physiol.* 285(2003):C370-C376.
Lipton et al. "Developmental Fate of Skeletal Satellite Cells." *Science.* 205(1979):1292-1294.
Liu. "Dendritic Cell Subsets and Lineages, and Their Functions in Innate and Adaptive Immunity." *Cell.* 106.3(2001):259-262.
Lu et al. "Muscle-Derived Stem Cells Seeded Into Acellular Scaffolds Develop Calcium-Dependent Contractile Activity That is Modulated by Nicotinic Receptors." *Urology.* 61(2003):1285-1291.
Lubeck. "The Costs of Musculoskeletal Disease: Health Needs Assessment and Health Economics." *Best Pract. Res. Clin. Rheumatol.* 17.3(2003):529-539.
Lumelsky et al. "Differentiation of Embryonic Stem Cells to Insulin-Secreting Structures Similar to Pancreatic Islets." *Science.* 292.5520(2001):1389-1394.
Mach et al. "Differences in Dendritic Cells Stimulated in Vivo by Tumors Engineered to Secrete Granulocyte-Macrophage Colony-Stimulating Factor or Flt3-Ligand." *Cancer Res.* 60.12(2000):3239-3246.
Magram et al. "IL-12-Deficient Mice are Defective but not Devoid of Type 1 Cytokine Responses." *Ann. N.Y. Acad. Sci.* 795(1996):60-70.
Maini. "Spatial and Spatio-Temporal Patterns in a Cell-Haptotaxis Model." *J. Math. Biol.* 27.5(1989):507-522.
Maley et al. "Extracellular Matrix, Growth Factors, Genetics: Their Influence on Cell Proliferation and Myotube Formation in Primary Cultures of Adult Mouse Skeletal Muscle." *Exp. Cell Res.* 219.1(1995):169-179.
Martinsen et al. "Alginate as Immobilization Material." *Biotech. Bioeng.* 33.1(1989):79-89.
Massia et al. "An RGD Spacing of 440 nm is Sufficient for Integrin $\alpha v \beta 3$-Mediated Fibroblast Spreading and 140 nm for Focal Contact and Stress Fiber Formation." *J. Cell Biol.* 114.5(1991):1089-1100.
Matthew et al. "Subperiosteal Behaviour of Alginate and Cellulose Wound Dressing Materials." *Biomaterials.* 16.4(1995):275-278.
McKinney-Freeman et al. "Muscle-Derived Hematopoietic Stem Cells are Hematopoietic in Origin." *PNAS.* 99.3(2002):1341-1346.
McPherron et al. "Regulation of Skeletal Muscle Mass in Mice by a New TGF-$\beta$ Superfamily Member." *Nature.* 387(1997):83-90.
Melero-Martin et al. "Engineering Robust and Functional Vascular Networks In Vivo With Human Adult and Cord Blood-Derived Progenitor Cells." *Circ. Res.* 103.2(2008):194-202.
Mellman et al. "Dendritic Cells: Specialized and Regulated Antigen Processing Machines." *Cell.* 106.3(2001):255-258.
Menetrey et al. "Suturing Versus Immobilization of a Muscle Laceration: A Morphological and Functional Study in a Mouse Model." *Am. J. Sports Med.* 27.2(1999):222-229.

Meyer et al. "Clinical Investigations of Toll-Like Receptor Agonists." *Expert Opin. Investig. Drugs.* 17.7(2008):1051-1065.
Meylan et al. "Intracellular Pattern Recognition Receptors in the Host Response." *Nature.* 442.7098(2006):39-44.
Miller et al. "Hepatocyte Growth Factor Affects Satellite Cell Activation and Differentiation in Regenerating Skeletal Muscle." *Am. J. Physiol. Cell Physiol.* 278(2000):C174-C181.
Mitchell et al. "The Exogenous Administration of Basic Fibroblast Growth Factor to Regenerating Skeletal Muscle in Mice Does Not Enhance the Process of Regeneration." *Growth Factors.* 13.1-2(1996):37-55.
Moioli et al. "Matrices and Scaffolds for Drug Delivery in Dental, Oral and Craniofacial Tissue Engineering." *Adv. Drug Deliv. Rev.* 59.4-5(2007):308-324.
Mooney et al. "Switching From Differentiation to Growth in Hepatocytes: Control by Extracellular Matrix." *J. Cell. Phys.* 151.3(1992):497-505.
Moser et al. "Dendritic Cell Regulation of TH1-TH2 Regulation." *Nat. Immunol.* 1.3(2000):199-205.
Naik et al. "Development of Plasmacytoid and Conventional Dendritic Cell Subtypes From Single Precursor Cells Derived in vitro and in vivo." *Nat. Immunol.* 8.11(2007):1217-1226.
Nair et al. "Polymers as Biomaterials for Tissue Engineering and Controlled Drug Delivery." *Adv. Biochem. Eng. Biotechnol.* 102(2006):47-90.
NCBI Accession No. NM_000758, Apr. 1, 2012.
NCBI Accession No. NM_003265, Dec. 30, 2012.
NCBI Accession No. NM_017442, Apr. 14, 2012.
NCBI Accession No. NP_000749.2, Apr. 1, 2012.
NCBI Accession No. NP_001020537, Jan. 30, 2011.
NCBI Accession No. NP_001020538, Jan. 30, 2011.
NCBI Accession No. NP_001020539, Jan. 30, 2011.
NCBI Accession No. NP_001020540, Jan. 30, 2011.
NCBI Accession No. NP_001028928, Jan. 30, 2011.
NCBI Accession No. NP_003367, Jan. 30, 2011.
NCBI Accession No. NP_059138, Apr. 14, 2012.
Nehls et al. "A Novel, Microcarrier-Based in Vitro Assay for Rapid and Reliable Quantification of Three-Dimensional Cell Migration and Angiogenesis." *Microvasc. Res.* 50.3(1995):311-322.
Noguera-Troise et al. "Blockade of Dll4 Inhibits Tumour Growth by Promoting Non-Productive Angiogenesis." *Nature.* 444.7122(2006):1032-1037.
O'Garra et al. "Are Dendritic Cells Afraid of Commitment?" *Nat. Immunol.* 5.12(2004):1206-1208.
O'Shea et al. "Type 1 IFNs and Regulation of TH1 Responses: Enigmas Both Resolved and Emerge." *Nat. Immunol.* 1.1(2000):17-19.
Ohlstein et al. "The Stem Cell Niche: Theme and Variations." *Curr. Opin. Cell Biol.* 16.6(2004):693-699.
Oldenburg et al. "TLR13 Recognizes Bacterial 23S rRNA Devoid of Erythromycin Resistance-Forming Modification." *Science.* 337.6098(2012):1111-1115.
Oldenhove et al. "Decrease of Foxp3+ Treg Cell Number and Acquisition of Effector Cell Phenotype During Lethal Infection." *Immunity.* 31.5(2009):772-786.
Ota et al. "Percutaneous Subxiphoid Access to the Epicardium Using a Miniature Crawling Robotic Device." *Innovations.* 1.5(2006):227-231.
Overwijk et al. "Tumor Regression and Autoimmunity After Reversal of a Functionally Tolerant State of Self-Reactive CD8+ T Cells." *J. Exp. Med.* 198.4(2003):569-580.
Ozawa et al. "Microenvironmental VEGF Concentration, Not Total Dose, Determines a Threshold Between Normal and Aberrant Angiogenesis." *J. Clin. Invest.* 113.4(2004):516-527.
Padilla et al. "Insufficient TLR Activation Contributes to the Slow Development of CD8+ T Cell Responses in *Trypanosoma cruzi* Infection." *J. Immunol.* 183(2009):1245-1252.
Palacio et al. "Interleukin 10 and Tumor Necrosis Factor $\alpha$ Gene Expression in Respiratory and Peripheral Muscles." *Arch. Bronconeumol.* 38.7(2002):311-316. (Spanish Original and English Abstract).

(56) References Cited

OTHER PUBLICATIONS

Partridge et al. "Conversion of mdx Myofibres From Dystrophin-Negative to -Positive by Injection of Normal Myoblasts." *Nature.* 337(1989):176-179.
Pelinkovic et al. "Tissue Engineering and Gene Therapy of the Muscoskeletal System with Muscle Cells." *Z. Orthop. Ihre Grenzgeb.* 138.5(2000):402-406.
Peters et al. "Engineering Vascular Networks in Porous Polymer Matrices." *J. Biomed. Mater. Res.* 60.4(2002):668-678.
Phillippi. "Patterning of Multiple Cell Lineages from a Single Stem Cell Population." *Annual Meeting of the American Society for Cell Biology.* (Dec. 10, 2006).
Pluen et al. "Role of Tumor-Host Interactions in Interstitial Diffusion of Macromolecules: Cranial vs. Subcutaneous Tumors." *PNAS.* 98.8(2001):4628-4633.
Pooyan et al. "Conjugates Beating Multiple Formyl-Methionyl Peptides Display Enhanced Binding to, but not Activation of Phagocytic Cells." *Bioconjugate Chem.* 13.2(2002):216-223.
Pope et al. "Organ-Specific Regulation of the CD8 T Cell Response to *Listeria monocytogenes* Infection." *J. Immunol.* 166(2001):3402-3409.
Pouzet et al. "Factors Affecting Functional Outcome After Autologous Skeletal Myoblast Transplantation." *Ann. Thorac. Surg.* 71(2001):844-851.
Pulendran et al. "Flt3-Ligand and Granulocyte Colony-Stimulating Factor Mobilize Distinct Human Dendritic Cell Subsets In Vivo." *J. Immunol.* 165(2000):566-572.
Qu et al. "Development of Approaches to Improve Cell Survival in Myoblast Transfer Therapy." *J. Cell Biol.* 142.5(1998):1257-1267.
Qu-Petersen et al. "Identification of a Novel Population of Muscle Stem Cells in Mice: Potential for Muscle Regeneration." *J. Cell Biol.* 157.5(2002):851-864.
Quezada et al. "CTLA4 Blockade and GM-CSF Combination Immunotherapy Alters the Intratumor Balance of Effector and Regulatory T Cells." *J. Clin. Invest.* 116.7(2006):1935-1945.
Rajagopalan et al. "Regional Angiogenesis With Vascular Endothelial Growth Factor in Peripheral Arterial Disease: A Phase II Randomized, Double-Blind, Controlled Study of Adenoviral Delivery of Vascular Endothelial Growth Factor 121 in Patients With Disabling Intermittent Claudication." *Circulation.* 108.16(2003):1933-1938.
Randolph et al. "Migration of Dendritic Cell Subsets and Their Precursors." *Annu. Rev. Immunol.* 26(2008):293-316.
Rappolee et al. "Macrophage-Derived Growth Factors." *Curr. Top. Microbiol. Immunol.* 181(1992):87-140.
Rapraeger. "Syndecan-Regulated Receptor Signaling." *J. Cell. Biol.* 149(2000):995-998.
Reddy et al. "Exploiting Lymphatic Transport and Complement Activation in Nanoparticle Vaccines." *Nat. Biotechnol.* 25.10(2007):1159-1164.
Reimann et al. "Satellite Cells in Normal and Regenerated Soleus Muscles of mdx and Control Mice." *Eur. J. Neurosci.* 10(1998):366. (Abstract #153.07).
Richards Grayson et al. "Multi-Pulse Drug Delivery From a Resorbable Polymeric Microchip Device." *Nat. Mater.* 2.11(2003):767-772.
Richardson et al. "Polymeric System for Dual Growth Factor Delivery." *Nat. Biotech.* 19.11(2001):1029-1034.
Riddle et al. "Role of Poly(lactide-co-glycolide) Particle Size on Gas-Foamed Scaffolds." *J. Biomater. Sci. Polym. Ed.* 15.12(2004):1561-1570.
Ridgway et al. "Inhibition of Dll4 Signalling Inhibits Tumour Growth by Deregulating Angiogenesis." *Nature.* 444.7122(2006):1083-1087.
Rinderknecht et al. "The Amino Acid Sequence of Human Insulin-Like Growth Factor I and its Structural Homology with Proinsulin." *J. Biol. Chem.* 253.8(1978):2769-2776.
Rosenberg et al. "Cancer Immunotherapy: Moving Beyond Current Vaccines." *Nat. Med.* 10.9(2004):909-915.
Roth et al. "SC68896, a Novel Small Molecule Proteasome Inhibitor, Exerts Antiglioma Activity In vitro and In vivo." *Clin. Cancer Res.* 15.21(2009):6609-6618.
Rowlands et al. "Directing Osteogenic and Myogenic Differentiation of MSCs: Interplay of Stiffness and Adhesive Ligand Presentation." *Am. J. Physiol Cell Physiol.* 295(2008): 1037-1044.
Rowley et al. "Alginate Type and RGD Density Control Myoblast Phenotype." *J. Biomed. Mater. Res.* 60.2(2002):217-233.
Rowley et al. "Biomaterials to Spatially Regulate Cell Fate." *Adv. Mater.* 14.12(2002):886-889.
Rowley. "Alginate Hydrogels as Synthetic Extracellular Matrix Materials." *Biomaterials.* 20.1(1999):45-53.
Rubin et al. "Dissociation of Heparan Sulfate and Receptor Binding Domains of Hepatocyte Growth Factor Reveals That Heparan Sulfate-c-Met Interaction Factilitates Signaling." *J. Biol. Chem.* 276.35(2001):32977-32983.
Ryten et al. "Atp Regulates the Differentiation of Mammalian Skeletal Muscle by Activation of a P2X5 Receptor on Satellite Cells." *J. Cell. Biol.* 158.2(2002):345-355.
Ryu et al. "The Construction of Three-Dimensional Micro-Fluidic Scaffolds of Biodegradable Polymers by Solvent Vapor Based Bonding of Micro-Molded Layers." *Biomaterials.* 28.6(2007):1174-1184.
Sano et al. "Swift Development of Protective Effector Functions in Naive CD8+ T Cells Against Malaria Liver Stages." *J. Exp. Med.* 194.2(2001):173-179.
Sansonetti. "The Innate Signaling of Dangers and the Dangers of Innate Signaling." *Nat. Immunol.* 7.12(2006):1237-1242.
Saxena et al. "Skeletal Muscle Tissue Engineering Using Isolated Myoblasts on Synthetic Biodegradable Polymers: Preliminary Studies." *Tissue Eng.* 5.6(1999):525-532.
Schaefer et al. Innate mmunity in the Human Female Reproductive Tract: Antiviral Response of Uterine Epithelial Cells to TLR3 Agonist Poly(I:C). *J. Immunol.* 174(2005):992-1002.
Schijns et al. "Mice Lacking IL-12 Develop Polarized Th1 Cells During Viral Infection." *J. Immunol.* 160(1998):3958-3964.
Schnorrer et al. "The Dominant Role of CD8+ Dendritic Cells in Cross-Presentation is not Dictated by Antigen Capture." *PNAS.* 103.28(2006):10729-10734.
Schuler et al. "The Use of Dendritic Cells in Cancer Immunotherapy." *Curr. Opin. Immunol.* 15.2(2003):138-147.
Seale et al. "Pax7 is Required for the Specification of Myogenic Satellite Cells." *Cell.* 102.6(2000):777-786.
Shansky et al. "Letter to the Editor: A Simplified Method for Tissue Engineering Skeletal Muscle Organoids In Vitro." *In Vitro Cell. Dev. Biol.* 33(1997):659-661.
Sheehan et al. "Skeletal Muscle Satellite Cell Proliferation in Response to Members of the Fibroblast Growth Factor Family and Hepatocyte Growth Factor." *J. Cell. Physiol.* 181.3(1999):499-506.
Sheridan et al. "Bioabsorbable Polymer Scaffolds for Tissue Engineering Capable of Sustained Growth Factor Delivery." *J. Control. Release.* 64.1-3(2000):91-102.
Shi et al. "A Novel Toll-Like Receptor that Recognizes Vascular Stomatitis Virus." *J. Biol. Chem.* 286.6(2011):4517-4524.
Shortman et al. "Steady-State and Inflammatory Dendritic-Cell Development." *Nat. Rev. Immunol.* 7(2007):19-30.
Sick et al. "WNT and DKK Determine Hair Follicle Spacing Through a Reaction-Diffusion Mechanism." *Science.* 314.5804(2006):1447-1450.
Silva et al. "Spatiotemporal Control of Vascular Endothelial Growth Factor Delivery From Injectable Hydrogels Enhances Angiogenesis." *J. Thromb. Haemost.* 5.3(2007):590-598.
Skokos et al. "CD8-DCs Induce IL-12-Independent Th1 Differentiation Through Delta 4 Notch-Like Ligand in Response to Bacterial LPS." *J. Exp. Med.* 204.7(2007):1525-1531.
Skuk et al. "Efficacy of Myoblast Transplantation in Nonhuman Primates Following Simple Intramuscular Cell Injections: Toward Defining Strategies Applicable to Humans." *Exp. Neurol.* 175.1(2002):112-126.
Skuk et al. "Myoblast Transplantation: The Current Status of a Potential Therapeutic Tool for Myopathies." *J. Musc. Res. Cell. Motil.* 24.4-6(2003):285-300.

(56) References Cited

OTHER PUBLICATIONS

Smidsrød et al. "Alginate as Immobilization Matrix for Cells." *Trends Biotechnol.* 8.3(1990):71-78.
Sohier et al. "Critical Factors in the Design of Growth Factor Releasing Scaffolds for Cartilage Tissue Engineering." *Exp. Opin. Drug Deliv.* 5.5(2008):543-566.
Steinman et al. "Taking Dendritic Cells into Medicine." *Nature.* 449.7161(2007):419-426.
Storrie et al. "Sustained Delivery of Plasmid DNA From Polymeric Scaffolds for Tissue Engineering." *Adv. Drug Deliv. Rev.* 58.4(2006):500-514.
Straub et al. "Animal Models for Muscular Dystrophy Show Different Patterns of Sarcolemmal Distruption." *J. Cell Biol.* 139.2(1997):375-385.
Sun et al. "Sustained Vascular Endothelial Growth Factor Delivery Enhances Angiogenesis and Perfusion in Ischemic Hind Limb." *Pharm. Res.* 22.7(2005):1110-1116.
Takeshita et al. "Therapeutic Angiogenesis." *J. Clin. Invest.* 93.2(1994):662-670.
Tamura et al. "Immunotherapy of Tumors with Autologous Tumor-Derived Heat Shock Protein Preparations." *Science.* 278.3(1997):117-120.
Tatsumi et al. "HGF/SF Is Present in Normal Adult Skeletal Muscle and Is Capable of Activating Satellite Cells." *Dev. Biol.* 194.1(1998):114-128.
Thurston et al. "The Delta Paradox: DLL4 Blockade Leads to More Tumour Vessels but Less Tumour Growth." *Nat. Rev. Cancer.* 8.5(2007):327-331.
Tidball. "Inflammatory Cell Response to Acute Muscle Injury." *Med. Sci. Sports Exerc.* 27.7(1995):1022-1032.
Turing. "Discussion: Turing's Theory of Morphogenesis—It's Influence on Modelling Biological Pattern and Form." *Bull. Math. Biol.* 52.1-2(1990):119-159.
Turing. "The Chemical Basis of Morphogenesis." *Philosophical Transactions of the Royal Society of London. Series B.* 237.641(1952):37-72.
Uchida et al. "Immunization by Particle Bombardment of Antigen-Loaded poly-(DL-lactide-co-glycolide) Microspheres in Mice." *Vaccine.* 12(2006):2120-2130.
Urbanek et al. "Stem Cell Niches in the Adult Mouse Heart." *PNAS.* 103.24(2006):9226-9231.
van Duin et al. "Triggering TLR Signaling in Vaccination." *Trends Immunol.* 27.1(2006):49-55.
Vandenburgh et al. "Tissue-Engineered Skeletal Muscle Organoids for Reversible Gene Therapy." *Hum. Gene Ther.* 17(1996):2195-2200.
Vieira et al. "The Bulk of Endogenously Produced IgG2a is Eliminated From the Serum of Adult C57BL/6 Mice With a Half-Life of 6-8 Days." *Eur. J. Immunol.* 16.7(1986):871-874.
Vieira et al. "The Half-Lives of Serum Immunoglobulins in Adult Mice." *Eur. J. Immunol.* 18.2(1988):313-316.
Villadangos et al. "Intrinsic and Cooperative Antigen-Presenting Functions of Dendritic-Cell Subsets in vivo." *Nat. Rev. Immunol.* 7.7(2007):543-555.
Villadangos. "Presentation of Antigens by MHC Class II Molecules: Getting the Most Out of Them." *Molec. Immunol.* 38.5(2001):329-346.
von Dassow et al. "The Segment Polarity Network is a Robust Developmental Module." *Nature.* 406.6792(2000):188-192.
Wakim et al. "Dendritic Cell-Induced Memory T Cell Activation in Nonlymphoid Tissues." *Science.* 319(2008):198-202.
Waldron-Lynch et al. "Advances in Type 1 Diabetes Therapeutics: Immunomodulation and β-Cell Savage." *Endocrinol. Metab. Clin. North Am.* 38.2(2009):303-317.
Wan et al. "Peritoneal Macrophage Uptake, Pharmacokinetics and Biodistribution of Macrophage-Targeted PEG-fMLF (N-Formyl-Methionyl-Leucyl-Phenylalanine) Nanocarriers for Improving HIV Drug Delivery." *Pharm. Res.* 24.11(2007):2110-2119.
Wang et al. "Biological Activity of Bevacizumab, a Humanized Anti-VEGF Antibody in vitro." *Angiogenesis.* 7.4(2004):335-345.

Wei et al. "Global Mapping of H3K4me3 and H3K27me3 Reveals Specificity in Plasticity in Lineage Fate Determination of Differentiating CD4+ T Cells." *Immunity.* 30.1(2009):155-167.
Wernig et al. "Function of Skeletal Muscle Tissue Formed After Myoblast Transplantation into Irradiated Mouse Muscles." *J. Physiol.* 522.2(2000):333-345.
White et al. "Leukemia Inhibitory Factor Enhances Regeneration in Skeletal Muscles After Myoblast Transplantation." *Musc. Nerve.* 24.5(2001):695-697.
World Health Organization. "Global Burden of Musculoskeletal Disease Revealed in new WHO Report." *Bull. World Health Organ.* 81.11(2003):853-854.
World Health Organization. "The World Health Report 2004: Changing History." *The World Health Report.* (2004):1-169.
Wright et al. "Muscle-Based Gene Therapy and Tissue Engineering for the Musculoskeletal System." *Drug Disc. Today.* 6.14(2001):728-733.
Yancopoulos et al. "Vascular-Specific Growth Factors and Blood Vessel Formation." *Nature.* 407.6801(2000):242-248.
Yuen et al. "Mimicking Nature by Codelivery of Stimulant and Inhibitor to Create Temporally Stable and Spatially Restricted Angiogenic Zones." *PNAS.* 107.42(2010):17933-17938.
Zammit et al. "Kinetics of Myoblast Proliferation Show That Resident Satellite Cells are Competent to Fully Regenerate Skeletal Muscle Fibers." *Exp. Cell Res.* 281.1(2002):39-49.
Zammit et al. "Muscle Satellite Cells Adopt Divergent Fates: A Mechanism for Self-Renewal?" *J. Cell Biol.* 166.3(2004):347-357.
Zeltinger et al. "Effect of Pore Size and Void Fraction on Cellular Adhesion, Proliferation, and Matrix Deposition." *Tissue Eng.* 7.5(2001):557-572.
Zhang et al. "A Comparative Study of the Antigen-Specific Immune Response Induced by Co-Delivery of CpG OGN and Antigen Using Fusion Molecules or Biodegradable Microparticles." *J. Pharma. Sci.* 98.12(2007):3283-3292.
Zhao et al. "Active Scaffolds for On-Demand Drug and Cell Delivery." *PNAS.* 108.1(2011):67-72.
Zhao et al. "Directed Cell Migration via Chemoattractants Released from Degradable Microspheres." *Biomat.* 26(2005):5048-5063.
Zhou et al. "Microstructure and Mechanical Properties of Poly(L-lactide) Scaffolds Fabricated by Gelatin Particle Leaching Method." *J. Appl. Polymer Sci.* 98(2005):1373-1379.
"Collagen: The Fibrous Proteins of the Matrix." *Molecular Cell Biology.* Lodish et al., eds. New York: W.H. Freeman. Section 22.3(2000):979-985.
Agache et al. "Mechanical Properties and Young's Modulus of Human Skin in Vivo." *Arch. Dermatol. Res.* 269.3(1980):221-232.
Aguado et al. "Improving Viability of Stem Cells During Syringe Needle Flow Through the Design of Hydrogel Cell Carriers." *Tissue Eng. Part A.* 18.7-8(2012):806-815.
Akpalo et al. "Fibrin-Polyethylene Oxide Interpenetrating Polymer Networks: New Self-Supported Biomaterials Combining the Properties of Both Protein Gel and Synthetic Polymer." *Acta Biomater.* 7.6(2011):2418-2427.
American Diabetes Association. "Standards of Medical Care in Diabetes—2013." *Diabetes Care.* 36.S1(2013):S11-S66.
Annaidh et al. "Characterization of the Anistropic Mechanical Properties of Excised Human Skin." *J. Mech. Behav. Biomed. Mater.* 5.1(2012):139-148.
Aschner et al. "Metabolic Memory for Vascular Disease in Diabetes." *Diabetes Technol. Ther.* 14.S1(2012):S68-S74.
Aubin et al. "Directed 3D Cell Alignment and Elongation in Microengineered Hydrogels." *Biomater.* 31.27(2010):6941-6951.
Babensee et al. "Host Response to Tissue Engineered Device." *Adv. Drug Deli. Rev.* 33.1-2(1998):111-139.
Becker et al. "Cytological Demonstration of the Clonal Nature of Spleen Colonies Derived from Transplanted Mouse Marrow Cells." *Nature.* 197(1963):452-454.
Bell. "Models for the Specific Adhesion of Cells to Cells." *Science.* 200.4342(1978):618-627.
Bencherif et al. "Influence of Cross-Linker Chemistry on Release Kinetics of PEG-co-PGA Hydrogels." *J. Biomed. Mater. Res. A.* 90.1(2009):142-153.

(56) References Cited

OTHER PUBLICATIONS

Bencherif et al. "End-Group Effects on the Properties of PEG-co-PGA Hydrogels." *Acta Biomater.* 5.6(2009):1872-1883.
Bencherif et al. "Influence of the Degree of Methacrylation of Hyaluronic Acid Hydrogels Properties." *Biomater.* 29.12(2008):1739-1749.
Bencherif et al. "Injectable Preformed Scaffolds with Shape-Memory Properties." *PNAS.* 109.48(2012):19590-19595.
Bencherif et al. "Nanostructured Hybrid Hydrogels Prepared by a Combination of Atom Transfer Radical Polymerization and Free Radical Polymerization." *Biomater.* 30.29(2009):5270-5278.
Bencherif et al. "Synthesis by AFET ATRP of Degradable Nanogel Precursors for in situ Formation of Nanostructured Hyaluronic Acid Hydrogel." *Biomacromol.* 10.9(2009):2499-2507.
Benton et al. "Photocrosslinking of Gelatin Macromers to Synthesize Porous Hydrogels that Promote Valvular Interstitial Cell Function." *Tissue Eng. Part A.* 15.11(2009):3221-3230.
Berg et al. "IL-10 is a Central Regulator of Cyclooxygenase-2 Expression and Prostaglandin Production." *J. Immunol.* 166.4(2001):2674-2680.
Bergstraesser et al. "Stimulation and Inhibition of Human Mammary Epithelial Cell Duct Morphogenesis In Vitro." *Proc. Assoc. Am. Physicians.* 108.2(1996):140-154.
Bianco et al. "The Meaning, the Sense and the Significance: Translating the Science of Mesenchymal Stem Cells into Medicine." *Nat. Med.* 19.1(2013):35-42.
Bilodeau et al. "Regular Pyramid Punch Problem." *J. Appl. Mech.* 59.3(1992):519-523.
Boateng et al. "Wound Healing Dressings and Drug Delivery Systems: A Review." *J. Pharm. Sci.* 97.8(2008):2892-2923.
Boerckel et al. "Mechanical Regulation of Vascular Growth and Tissue Regeneration in vivo." *PNAS.* 108.37(2011):E674-E680.
Boontheekul et al. "Controlling Alginate Gel Degradation Utilizing Partial Oxidation and Bimodal Molecular Weight Distribution." *Biomaterials.* 26.15(2005):2455-2465.
Brignone et al. "A Phase I Phamacokinetic and Biological Correlative Study of IMP321, a Novel MHC Class II Agonist, in Patients with Advanced Renal Cell Carcinoma." *Clin. Cancer Res.* 15.19(2009):6225-6231.
Broxmeyer et al. "Insights into the Biology of Cord Blood Stem/Progenitor Cells." *Cell Prolif.* 44.S1(2011):55-59.
Buckwalter et al. "Form of Antigen Dictates Immunity: Irradiated Cell vs. Whole Cell Lysate Vaccination." *J. Immunol.* 178(2007).
Bullard et al. "Fetal Wound Healing: Current Biology." *World J. Surg.* 27.1(2003):54-61.
Buonaguro et al. "Translating Tumor Antigens into Cancer Vaccines." *Clin. Vaccine Immunol.* 18.1(2011):23-34.
Burdick et al. "Controlled Degradation and Mechanical Behavior of Photopolymerized Hyaluronic Acid Networks." *Biomacromol.* 6.1(2005):386-391.
Burdick et al. "Photoencapsulation of Osteoblasts in Injectable RGD-Modified PEG Hydrogels for Bone Tissue Engineering." *Biomater.* 23.22(2002):4315-4323.
Bégué et al. "Vaccination Against Human Papillomavirus. Implementation and Efficacy Against Cervical Cancer Control." *Bull. Acad. Natl. Med.* 191.9(2007):1805-1816. (French original and English abstract).
Burger et al. "Effect of VEGF and its Receptor Antagonist SU-5416, an Inhibitor of Angiogenesis, on Processing of the β-amyloid Precursor Protein in Primary Neuronal Cells Derived From Brain Tissue of Tg2576 Mice." *Int. J. Dev. Neurosci.* 28.7(2010):597-604.
Cameron et al. "The Influence of Substrate Creep on Mesenchymal Stem Cell Behaviour and Phenotype." *Biomater.* 32.26(2011):5979-5993.
Caulfield et al. "Regulation of Major Histocompatibility Complex Class II Antigens on Human Alveolar Macrophages by Granulocyte-Macrophage Colony-Stimulating Factor in the Presence of Glucocorticoids." *Immunol.* 98.1(1999):104-110.

Ceriello et al. "The 'Metabolic Meory': Is more than just Tight Glucose Control Necessary to Prevent Diabetic Complications?" *J. Clin. Endocrinol. Metab.* 94.2(2009):410-415.
Ceriello et al. "The Emerging Challenge in Diabetes: The 'Metabolic Memory.'" *Vascular Pharmacol.* 57.5-6(2012):133-138.
Chan et al. "Traction Dynamics of Filopodia on Compliant Substrates." *Science.* 322.5908(2008):1687-1691.
Chang. "Mouse Models for Studies of Retinal Degeneration and Diseases." *Methods Mol. Biol.* 935(2013):27-39.
Chen et al. "Functional Human Vascular Network Generated in Photocrosslinkable Gelatin Methacrylate Hydrogels." *Adv. Funct. Mater.* 22.10(2012):2027-2039.
Chiang et al. "Whole Tumor Antigen Vaccines." *Semin. Immunol.* 22.3(2010):132-143.
Choi et al. "In Vitro Mineralization by Preosteoblasts in Poly(DL-lactide-co-glycolide) Inverse Opal Scaffolds Reinforced with Hydrozyapatite Nanoparticles." *Langmuir.* 26.14(2010):12126-12131.
Choi et al. "Three-Dimentional Scaffolds for Tissue Engineering: The Importance of Uniformity in Pore Size and Structure." *Langmuir.* 26.24(2010):19001-19006.
Chou et al. "Characterization of Photocross Linked Alginate Hydrogels for Nucleus Pulposus Cell Encapsulation." *J. Biomed. Mater. Res. A.* 91A.1(2009):187-194.
Clark et al. "Myosin II and Mechanotransduction: A Balancing Act." *Trends Cell Biol.* 17.4(2007):178-186.
Comisar et al. "Engineering RGD Nanopatterned Hydrogels to Control Preosteoblast Behavior: A Combined Computational and Experimental Approach." *Biomaterials.* 28(2007):4409-4417.
Cook et al. "A Sialomucopeptide Liberated by Trypsin from the Human Erythrocyte." *Nature.* 188(1960):1011-1012.
Cooper. "Metabolic Memory: Implications for Diabetic Vascular Complications." *Pediatr. Diabetes.* 10.5(2009):343-346.
Cuda et al. "In Vitro Actin Filament Sliding Velocities Produced by Mixtures of Different Types of Myosin." *Biophys. J.* 72.4(1997):1767-1779.
Cukierman et al. "Taking Cell-Matrix Adhesions to the Third Dimension." *Science.* 294.5547(2001):1708-1712.
David et al. "The in vitro Desensitization of Sensitive Cells by Trypsin." *J. Exp. Med.* 120(1964):1189-1200.
Davies et al. "Antibody-Antigen Complexes." *Annu. Rev. Biochem.* 59(1990):439-473.
Dembo et al. "Stresses at the Cell-to-Substrate Interface During Locomotion of Fibroblasts." *Biophys. J.* 76.4(1999):2307-2316.
Dexter et al. "Conditions Controlling the Proliferation of Haemopoietic Stem Cells In Vitro." *J. Cell. Physiol.* 91.3(1977):335-344.
Di Nicola et al. "Human Bone Marrow Stromal Cells Suppress T-Lymphocyte Proliferation Induced by Cellular or Nonspecific Mitogenic Stimuli." *Blood.* 99.10(2002):3838-3843.
Diduch et al. "Two Cell Lines from Bone Marrow tht Differ in Terms of Collagen Synthesis, Osteogenic Characteristics, and Matrix Mineralization." *J. Bone Joint Surg. Am.* 75.1(1993):92-105.
Diridollou et al. "Skin Ageing: Changes of Physical Properties of Human Skin in vivo." *J. Cosmet. Sci.* 23.6(2001):353-362.
Discher et al. "Tissue Cells Feel and Respond to the Stiffness of their Substrate." *Science.* 310.5751(2005):1139-1143.
Disis et al. "Granulocyte-Macrophage Colony-Stimulating Factor: An Effective Adjuvant for Protein and Peptide-Based Vaccines." *Blood.* 88.1(1996):202-210.
Donati et al. "New Hypothesis on the Role of Alternating Sequences in Calcium-Alginate Gels." *Biomacromol.* 6.2(2005):1031-1040.
Douay et al. "Ex vivo Production of Human Red Blood Cells from Hematopoietic Stem Cells: What is the Future in Transfusion?" *Transfus. Med. Rev.* 21.2(2007):91-100.
Dranoff. "GM-CSF-Based Cancer Vaccines." *Immunol Rev.* 188(2002):147-154.
DuFort et al. "Balancing Forces: Architectural Control of Mechanotransduction." *Nat. Rev. Mol. Cell Biol.* 12.5(2011):308-319.
Dupont et al. "Role of YAP/TAZ in Mechanotransduction." *Nature.* 474.7350(2011):179-183.

(56) References Cited

OTHER PUBLICATIONS

Edwards et al. "Evaluation of Biomechanical Properties of Human Skin." *Clin. Dermatol.* 13.4(1995):375-380.
Eming et al. "Inflammation in Wound Repair: Molecular and Cellular Mechanisms." *J. Invest. Dermatol.* 127.3(2007):514-525.
Engler et al. "Microtissue Elasticity: Measurements by Atomic Force Microscopy and its Influence on Cell Differentiation." *Methods Cell. Biol.* 83(2007):521-545.
Engler et al. "Substrate Compliance Versus Ligand Density in Cell on Gel Response." *Biophys. J.* 86.1Pt1(2004):617-628.
Exposito et al. "The Fibrallar Collagen Family." *Int. J. Mol. Sci.* 11.2(2010):407-426.
Falanga. "Wound Healing and its Impairment in the Diabetic Foot." *Lancet.* 366.9498(2005):1736-1743.
Fauquemberque et al. "HLA-A*0201-Restricted CEA-Derived Peptide CAP1 is not a Suitable Target for T-Cell-Based Immunotherapy." *J. Immunother.* 33.4(2010):402-413.
Fisher et al. "The Study of Protein Mechanics with the Atomic Force Microscope." *Trends Biochem. Sci.* 24.10(1999):379-384.
Friedenstein et al. "Fibroblast Precursors in Normal and Irradiated Mouse Hematopoietic Organs." *Exp. Hematol.* 4.5(1976):267-274.
Gardel et al. "Traction Stress in Focal Adhesions Correlates Biphasically with Actin Retrograde Flow Speed." *J. Cell Biol.* 183.6(2008):999-1005.
Gasic et al. "Removal and Regeneration of the Cell Coating in Tumour Cells." *Nature.* 196(1962):170.
Gauthier et al. "Temporary Increase in Plasma Membrane Tension Coordinates the Activation of Exocytosis and Contraction During Cell Spreading." *PNAS.* 108.35(2011):14467-14472.
Geerligs et al. "Linear Viscoelastic Behavior of Subcutaneous Adipose Tissue." *Biorheol.* 45.6(2008):677-688.
GenBank Accession No. AAA36738.1, Aug. 3, 1993.
GenBank Accession No. AAA60022.1, Jan. 7, 1995.
GenBank Accession No. AAA64239.1, Mar. 23, 1995.
GenBank Accession No. AAB18786.3, Jul. 12, 1999.
GenBank Accession No. AAH94877.1, May 20, 2005.
GenBank Accession No. AE022039.1, Sep. 17, 2011.
GenBank Accession No. AF344424.1, Apr. 8, 2002.
GenBank Accession No. AF414120.1, Sep. 26, 2001.
GenBank Accession No. AF450242.1, Feb. 11, 2002.
GenBank Accession No. AJ583695.1, Oct. 7, 2008.
GenBank Accession No. AY291313.1, Apr. 26, 2004.
GenBank Accession No. BC094887.1, Jul. 21, 2006.
GenBank Accession No. CAA01955.1, Nov. 14, 2006.
GenBank Accession No. DQ103757.1, Jul. 25, 2005.
GenBank Accession No. JN602184.1, Sep. 17, 2011.
GenBank Accession No. M16006.1, Jan. 7, 1995.
GenBank Accession No. M24902.1, Jan. 7, 1995.
GenBank Accession No. M73239.1, Mar. 23, 1995.
GenBank Accession No. NM_000091.4, May 10, 2014.
GenBank Accession No. NM_000572.2, May 18, 2014.
GenBank Accession No. NM_000638.3, May 4, 2014.
GenBank Accession No. NM_000758.3, May 4, 2014.
GenBank Accession No. NM_000885.4, Apr. 13, 2014.
GenBank Accession No. NM_000963.3, Jun. 13, 2014.
GenBank Accession No. NM_001001522.1, May 18, 2014.
GenBank Accession No. NM_001845.4, May 3, 2014.
GenBank Accession No. NM_001901.2, May 18, 2014.
GenBank Accession No. NM_002421.3_05112014.
GenBank Accession No. NM_002982.3, May 3, 2014.
GenBank Accession No. NM_003377.4, May 5, 2014.
GenBank Accession No. NM_003392.4, May 5, 2014.
GenBank Accession No. NM_004469.4, May 25, 2014.
GenBank Accession No. NM_005429.3, Mar. 31, 2014.
GenBank Accession No. NM_015719.3, Feb. 26, 2014.
GenBank Accession No. NP_000082.2, May 10, 2014.
GenBank Accession No. NP_000629.3, May 4, 2014.
GenBank Accession No. NP_000749.2, May 4, 2014.
GenBank Accession No. NP_000876.3, Apr. 13, 2014.
GenBank Accession No. NP_000954.1, Jun. 13, 2014.
GenBank Accession No. NP_001001522.1, May 18, 2014.
GenBank Accession No. NP_001836.2, May 3, 2014.
GenBank Accession No. NP_001892.1, May 18, 2014.
GenBank Accession No. NP_002973.1, May 3, 2014.
GenBank Accession No. NP_003239.2, Feb. 18, 2014.
GenBank Accession No. NP_003368.1, May 5, 2014.
GenBank Accession No. NP_003383.2, May 5, 2014.
GenBank Accession No. NP_004460.1, May 25, 2014.
GenBank Accession No. NP_005420.1, May 11, 2014.
GenBank Accession No. NP_056534.2, Feb. 26, 2014.
GenBank Accession No. U76381.2, Jul. 12, 1999.
Genes et al. "Effect of Substrate Mechanics on Chondrocyte Adhesion to Modified Alginate Surfaces." *Arch. Biochem. Biophys.* 422.2(2004):161-167.
Graessley. "Entangled Linear, Branched and Network Polymer Systems—Molecular Theories." *Adv. Poly. Sci.* 47(1982):67-117.
Guillaume et al. "Two Abundant Proteasome Subtypes that Uniquely Process Some Antigens Presented by HLA Class I Molecules." *PNAS.* 107.43(2010):18599-18604.
Guo et al. "Droplet Microfluidics for High-Throughput Biological Assays." *Lab Chip.* 12.12(2012):2146-2155.
Gurkan et al. "The Mechanical Environment of Bone Marrow: A Review." *Ann. Biomed. Eng.* 36.12(2008):1978-1991.
Halim et al. "Biologic and Synthetic Skin Substitutes: An Overview." *Indian J. Plast. Surg.* 43(2010):S23-S28.
Harris. "Classification, Diagnostic Criteria, and Screening for Diabetes." *Diabetes in America.* NIH Publication No. 95-1468. Chapter 2. (1995):15-36.
Humphries et al. "Integrin Ligands at a Glance." *J. Cell. Sci.* 119.Pt19(2006):3901-3903.
Huston et al. "Protein Engineering of Antibody Binding Sites: Recovery of Specific Activity in an Anti-Digoxin Single-Chain Fv Analogue Produced in *Escherichia coli.*" *PNAS.* 85.16(1988):5879-5883.
Hutson et al. "Synthesis and Characterization of Tunable Poly(ethylene Glycol): Gelatin Methacrylate Composite Hydrogels." *Tissue Eng. Part A.* 17.13-14(2011):1713-1723.
Hwang et al. "Fabrication of Three-Dimensional Porous Cell-Laden Hydrogel for Tissue Engineering." *Biofabrication.* 2.3(2010):035003.
Ihnat et al. "Hypothesis: The 'Metabolic Memory', the New Challenge of Diabetes." *Diabet. Med.* 24.6(2007)582-586.
Isern et al. "Self-Renewing Human Bone Marrow Mesenspheres Promote Hematopoietic Stem Cell Expansion." *Cell Rep.* 3.5(2013):1714-1724.
Janmey et al. "From Tissue Mechanics to Transcription Factors." *Differentiation.* 86.3(2013):112-120.
Jiang et al. "Two-Piconewton Slip Bond Between Fibronectin and the Cytoskeleton Depends on Talin." *Nature.* 424.6946(2003):334-337.
Jokinen et al. "Integrin-Mediated Cell Adhesion to Type I Collagen Fibrils." *J. Biol. Chem.* 279.30(2004):31956-31963.
Jugdutt et al. "Aging and Defective Healing, Adverse Remodeling, and Blunted Post-Conditioning in the Reperfused Wounded Heart." *J. Am. Coll. Cardiol.* 51.14(2008):1399-1403.
Kang et al. "Effect of Porous Structure on the Degradation of Freeze-Dried Gelatin Hydrogels." *J. Bioact. Compat. Poly.* 14.4(1999):331-343.
Katayama et al. "Integrated Analysis of the Genome and the Transcriptome by FANTOM." *Brief Bioinform.* 5.3(2004):249-258.
Kearney et al. "Macroscale Delivery Systems for Molecular and Cellular Payloads." *Nat. Mater.* 12.11(2013):1004-10017.
Kennedy et al. "Rapid and Extensive Collapse from Electrically Responsive Macroporous Hydrogels." *Adv. Healthc. Mater.* 3.4(2014):500-507.
Khetan et al. "Degradation-Mediated Cellular Traction Directs Stem Cell Fate in Covalently Crosslinked Three-Dimensional Hydrogels." *Nat. Mater.* 12.5(2013):458-465.
Kim et al. "Multifunctional Capsule-in-Capsules for Immunoprotection and Trimodal Imaging." *Angew. Chem. Int. Ed.* 50.10(2011):2317-2321.
Klein et al. "Cell-Cycle Control by Physiological Matrix Elasticity and In Viivo Tissue Stiffening." *Curr. Biol.* 19.18(2009):1511-1518.

(56) References Cited

OTHER PUBLICATIONS

Kohane. "Microparticles and Nanoparticles for Drug Delivery." *Biotechnol. Bioeng.* 96.2(2007):203-209.
Kong et al. "FRET Measurements of Cell-Traction Forces and Nano-Scale Clustering of Adhesion Ligands Varied by Substrate Stiffness." *PNAS.* 102.12(2005):4300-4305.
Kratky et al. "Direct Activation of Antigen-Presenting Cells is Required for CD8+ T-Cell Priming and Tumor Vaccination." *PNAS.* 108.42(2011):17414-17419.
Kuwahara et al. "Cell Delivery Using an Injectable and Adhesive Transglutaminase-Gelatin Gel." *Tissue Eng. Part C Methods.* 16.4(2010):609-618.
Lee et al. "Intravenous hMSCs Improve Myocardial Infarction in Mice because Cells Embolized in Lung are Activated to Secrete the Anti-Inflammatory Protein TSG-6." *Cell Stem Cell.* 5.1(2009):54-63.
Lee et al. "Engineering Liver Tissue Spheroids with Inverted Colloidal Crystal Scaffolds." *Biomater.* 30.27(2009):4687-4694.
Lele et al. "Investigating Complexity of Protein-Protein Interactions in Focal Adhesions." *Biochem. Biophys. Res. Commun.* 369.3(2008):929-934.
Levental et al. "Soft Biological Materials and their Impact on Cell Function." *Soft Matter.* 3(2007):299-306.
Li et al. "A Novel Cyclohexene Derivate, Ethyl (6R)-6-[N-(2-Chloro-4-fluorophenyl)sulfamoyl]cyclohex-1-ene-1-carboxylate (TAK-242), Selectively Inhibits Toll-Like Receptor 4-Mediated Cytokine Production Through Suppression of Intracellular Signaling." *Mol. Pharmacol.* 69.4(2006):1288-1295.
Li et al. "Purified Hybrid Cells from Dendritic Cell and Tumor Cell Fusions are Superior Activators of Antitumor Immunity." *Cancer Immunol. Immunother.* 50.9(2001):456-462.
Lin et al. "Transdermal Regulation of Vascular Network Bioengineering Using a Photopolymerizable Methacrylated Gelatin Hydrogel." *Biomater.* 34.28(2013):6785-6796.
Liu et al. "On the Viscoelastic Character of Liver Tissue: Experiments and Modelling of the Linear Behaviour." *Biorheol.* 37.3(2000):191-201.
Lo et al. "Cell Movement is Guided by the Rigidity of the Substrate." *Biophys. J.* 79.1(2000):144-152.
Ludewig et al. "Immunotherapy with Dendritic Cells Directed Against Tumor Antigens Shared with Normal Host Cells Results in Severe Autoimmune Disease." *J. Exp. Med.* 191.5(2000):795-804.
Majeti et al. "Identification of a Hierarchy of Multipotent Hematopoietic Progenitors in Human Cord Blood." *Cell Stem Cell.* 1.6(2007):635-645.
Malmqvist. "Biospecific Interaction Analysis Using Biosensor Technology." *Nature.* 361.6408(1993):186-187.
Mammoto et al. "Mechanical Control of Tissue and Organ Development." *Development.* 137.9(2010):1407-1420.
Manavski et al. "Vascular Niche Controls Organ Regeneration." *Circ. Res.* 114.17(2014):1077-1079.
Mansoor et al. "Engineering T Cells for Cancer Therapy." *Br. J. Cancer.* 93.10(2005):1085-1091.
Masedunskas et al. "Role for the Actomyosin Complex in Regulated Exocytosis Revealed by Intravital Microscopy." *PNAS.* 108.33(2011):13552-13557.
McDonald et al. "Early Fracture Callus Displays a Smooth Muscle-Like Viscoelastic Properties Ex Viivo: Implications for Fracture Healing." *J. Orthop. Res.* 27.11(2009):1508-1513.
McKinnon et al. "Biophysically Defined and Cytocompatible Covalently Adaptable Networks as Viscoelastic 3D Cell Culture Systems." *Adv. Mater.* 26.6(2014):865-872.
McWhorter et al. "Modulation of Macrophage Phenotype by Cell Shape." *PNAS.* 110.43(2013):17253-17258.
Melief et al. "Immunotherapy of Established (Pre)Malignant Disease by Synthetic Long Peptide Vaccines." *Nat. Rev. Cancer.* 8(2008):351-360.
Merkel et al. "Using Mechanobiological Mimicry of Red Blood Cells to Extend Circulation Times of Hydrogel Microparticles." *PNAS.* 108.2(2011):586-591.
Metters et al. "Fundamental Studies of Biodegradable Hydrogels as Cartilage Replacement Materials." *Biomed. Sci. Instrum.* 35(1999):33-38.
Miller et al. "Melanoma." *N. Engl. J. Med.* 355.1(2006):51-65.
Miralles et al. "Actin Dynamics Control SRF Activity by Regulation of its Coactivator MAL." *Cell.* 113.3(2003):329-342.
Molinari et al. "Modification of Surface Membrane Antigens by Trypsin." *Proc. Soc. Exp. Biol. Med.* 148.4(1975):991-994.
Molloy et al. "Movement and Force Produced by a Single Myosin Head." *Nature.* 378.6553(1995):209-212.
Mooney et al. "Cytoskeletal Filament Assembly and the Control of Cell Spreading and Function by Extracellular Matrix." *J. Cell Sci.* 108(1995):2311-2320.
Muralidharan-Chari et al. "ARF6-Regulated Shedding of Tumor Cell-Derived Plasma Membrane Microvesicles." *Curr. Biol.* 19.22(2009):1875-1885.
NCBI Accession No. NM_001561.5, Mar. 16, 2014.
NCBI Accession No. NM_004448.3, Apr. 23, 2014.
NCBI Accession No. NM_005018.2, Apr. 27, 2014.
NCBI Accession No. NM_181780.3, Jan. 27, 2014.
NCBI Accession No. NP_001552.2, Mar. 16, 2014.
NCBI Accession No. NP_003237.2, May 25, 2014.
NCBI Accession No. NP_003318.1, May 4, 2014.
NCBI Accession No. NP_003327.3, May 4, 2014.
NCBI Accession No. NP_005009.2, Apr. 27, 2014.
NCBI Accession No. NP_861445.3, Jan. 27, 2014.
Nichol et al. "Cell-Laden Microengineered Gelatin Methacrylate Hydrogels." *Biomater.* 31.21(2010):5536-5544.
Nicodemus et al. "Cell Encapsulation in Biodegradable Hydrogels for Tissue Engineering Applications." *Tissue Eng. Part B Rev.* 14.2(2008):149-165.
Niessen et al. "The $\alpha 6\beta 4$ Integrin is a Receptor for Both Lamin and Kalinin." *Exp. Cell Res.* 211.2(1994):360-367.
Osunkoya et al. "Synthesis and Fate of Immunological Surface Receptors on Cultured Burkitt Lymphoma Cells." *Int. J. Cancer.* 4.2(1969):159-165.
Page-McCaw et al. "Matrix Metalloproteinases and the Regulation of Tissue Remodelling." *Nat. Rev. Mol. Cell Biol.* 8.3(2007):221-233.
Pailler-Mattei et al. "In vivo Measurements of the Elastic Mechanical Properties of Human Skin by Indentation Tests." *Med. Eng. Phys.* 30.5(2008):599-606.
Pardoll. "The Blockade of Immune Checkpoints in Cancer Immunotherapy." *Nat. Rev. Cancer.* 12.4(2012):252-264.
Parekh et al. "Modulus-Driven Differentiation of Marrow Stromal Cells in 3D Scaffolds that is Independent of Myosin-Based Cytoskeletal Tension." *Biomater.* 32.9(2011):2256-2264.
Parekkadan et al. "Mesenchymal Stem Cell-Derived Molecules Reverse Fulminant Hepatic Failure." *PLoS One.* 2.9(2007):e941.
Park et al. "Photopolymerized Hyaluronic Acid-Based Hydrogels and Interpenetrating Networks." *Biomater.* 24.6(2003):893-900.
Pawlaczyk et al. "Age-Dependent Biomechanical Properties of the Skin." *Postepy. Dermatol. Alergol.* 30.5(2013):302-306.
Pek et al. "The Effect of Matrix Stiffness on Mesenchymal Stem Cell Differentiation in a 3D Thixotropic Gel." *Biomater.* 31.3(2010):385-391.
Pena et al. "Effects of TGF-$\beta$ and TGF-$\beta$ Neutralizing Antibodies on Fibroblast-Induced Collagen Gel Contraction: Implications for Proliferative Vitroretinpathy." *Invest. Ophthalmol. Vis. Sci.* 35.6(1994):2804-2808.
Peyton et al. "The Use of Poly(ethylene glycol) Hydrogels to Investigate the Impact of ECM Chemistry and Mechanics on Smooth Muscle Cells." *Biomater.* 27.28(2006):4881-4893.
Pinho et al. "PDGFR$\alpha$ and CD51 Mark Human Nestin+ Sphere-Forming Mesenchymal Stem Cells Capable of Hematopoietic Progenitor Cell Expansion." *J. Exp. Med.* 210.7(2013):1351-1367.
Qi et al. "Patterned Differentiation of Individual Embryoid Bodies in Spatially Organized 3D Hybrid Microgels." *Adv. Mater.* 22.46(2010):5276-5281.
Qin et al. "Soft Lithography for Micro- and Nanoscale Patterning." *Nat. Protoc.* 5.3(2010):491-502.

(56) References Cited

OTHER PUBLICATIONS

Raeber et al. "Molecularly Engineered PEG Hydrogels: A Novel Model System for Proteolyrically Mediated Cell Migration." *Biophys. J.* 89.2(2005)1374-1388.
Ramón-Azcón et al. "Gelatin Methacrylate as a Promising Hydrogel for 3D Microscale Organization and Proliferation of Dielectroretically Patterned Cells." *Lab on a Chip.* 12.16(2012):2959-2969.
Ranganath et al. "Harnessing the Mesenchymal Stem Cell Secretome for the Treatment of Cardiovascular Disease." *Cell Stem Cell.* 10.3(2012):244-258.
Raposo et al. "Extracellular Vesicles: Exosomes, Microvesicles, and Friends." *J. Cell. Biol.* 200.4(2013):373-383.
Roccaro et al. "BM Mesenchymal Stromal Cell-Derived Exosomes Facilitate Multiple Myeloma Progression." *J. Clin. Invest.* 123.4(2013):1542-1555.
Rodriguez et al. "Minimal "Self" Peptides that Inhibit Phagocytic Clearance and Enhance Delivery of Nanoparticles." *Science.* 339.6122(2013):971-975.
Sacchetti et al. "Self-Renewing Osteoprogenitors in Bone Marrow Sinusoids can Organize a Hematopoietic Microenvironment." *Cell.* 131.2(2007):324-336.
Sakai et al. "An Injectable, in situ Enzymatically Gellable, Gelatin Derivative for Drug Delivery and Tissue Engineering." *Biomater.* 30.20(2009):3371-3377.
Scheel et al. "Toll-Like Receptor-Dependent Activation of Several Human Blood Cell Types by Protamine Condensed mRNA." *Eur. J. Immunol.* 35(2005):1557-1566.
Schofield. "The Relationship Between the Spleen Colony-Forming Cell and the Haemopoietic Stem Cell." *Blood. Cells.* 4.1-2(1978):7-25.
Schwartz. "Integrins and Extracellular Matrix in Mechanotransduction." *Cold Spring Harb. Perspect. Biol.* 2.12(2010):a005066.
Sensi et al. "Unique Tumor Antigens: Evidence for Immune Control of Genome Integrity and Immunogenic Targets for T Cell-Mediated Patient-Specific Immunotherapy." *Clin. Cancer Res.* 12.17(2006):5023-5032.
Shi et al. "Granulocyte-Macrophage Colony-Stimulating Factor (GM-CSF) and T-Cell Responses: What we do and don't know." *Cell Res.* 16.2(2006):126-133.
Shin et al. "Contractile Forces Sustain and Polarize Hematopoiesis from Stem and Progenitor Cells." *Cell Stem Cell.* 14.1(2014):81-93.
Shin et al. "Lamins Regulate Cell Trafficking and Lineage Maturation of Adult Human Hematopoetic Cells." *PNAS.* 110.47(2013):18892-18897.
Shin et al. "Myonsin-II Inhibition and Soft 2D Matrix Maximize Multinucleation and Cellular Projections Typical of Platelet-Producing Megakaryocytes." *PNAS.* 108.28(2011):11458-11463.
Siegwart et al. "Synthesis, Characterization, and in vitro Cell Culture Viability of Degradable Poly(N-isopropylacrylamide-co-5,6-benzo-2-methylene-1,3-dioxepane)-Based Polymers and Cross-linked Gels." *J. Biomed. Mater. Res. A.* 87.2(2008):345-358.
Silva et al. "Effects of VEGF Temporal and Spatial Presentation on Angiogenesis." *Biomaterials.* 31.6(2010):1235-1241.
Singer et al. "Cutaneous Wound Healing." *N. Engl. J. Med.* 341.10(1999):738-746.
Solon et al. "Fibroblast Adaptation and Stiffness Matching to Soft Elastic Substrates." *Biophys. J.* 93.12(2007):4453-4461.
Stachowiak et al. "Inverse Opal Hydrogel-Collagen Composite Scaffolds as a Supportive Microenvironment for Immune Cell Migration." *J. Biomed. Mater. Res.* 85A(2008):815-828.
Sun et al. "Biomimetic Interpenetrating Polymer Network Hydrogels Based on Methacrylated Alginate and Collagen for 3D Pre-Osteoblast Spreading and Osteogenic Differentiation." *Soft Matter.* 8(2012):2398-2404.
Sun et al. "Highly Stretchable and Tough Hydrogels." *Nature.* 489.7414(2012):133-136.
Suri et al. "Photopatterned Collagen-Hyaluronic Acid Interpenetrating Polymer Network Hydrogels." *Acta Biomater.* 5.7(2009):2385-2397.
Swift et al. "Nuclear Lamin-A Scales with Tissue Stiffness and Enhances Matrix-Directed Differentiation." *Science.* 341.6149(2013):1240104.
Syed et al. "Stem Cell Therapy Market." *Nat. Rev. Drug Discov.* 12.3(2013):185-186.
Tabata et al. "Enhanced Vascularization and Tissue Granulation by Basic Fibroblast Growth Factor Impregnated in Gelatin Hydrogels." *J. Control. Release.* 31.2(1994):189-199.
Tannous. "*Gaussia* Luciferase Reporter Assay for Monitoring Biological Processes in Culture and in vivo." *Nat. Protoc.* 4.4(2009):582-591.
Thomas et al. "Intravenous Infusion of Bone Marrow in Patients Receiving Radiation and Chemotherapy." *N. Engl. J. Med.* 257.11(1957):491-496.
Thurner et al. "Vaccination with Mage-3A1 Peptide-Pulsed Mature, Monocyte-Derived Dendritic Cells Expands Specific Cytotoxic T Cells Induces Regression of Some Metastases in Advanced Stage IV Melanoma." *J. Exp. Med.* 190.11(1999):1669-1678.
Tong et al. "Engineering Interpenetrating Network Hydrogels as Biomimetic Cell Niche with Independently Tunable Biochemical and Mechanical Properties." *Biomater.* 35.6(2014):1807-1815.
Trappmann et al. "Extracelluar-Matrix Tethering Regulates Stem-Cell Fate." *Nat. Mater.* 11.7(2012):642-649.
Trappmann et al. "How Cells Sense Extracellular Matrix Stiffness: A Material's Perspective." *Curr. Opin. Biotechnol.* 24.5(2013):948-953.
Uhlenbruck. "Action of Proteolytic Enzymes on the Human Erythrocyte Surface." *Nature.* 190(1961):181.
Ulrich et al. "Probing Cellular Mechanobiology in Three-Dimensional Culture with Collagen-Agarose Matrices." *Biomater.* 31.7(2010):1875-1884.
UniProtKB/Swiss-Prot Accession No. P02751.4, Apr. 16, 2014.
UniProtKB/Swiss-Prot Accession No. P02778.2, Jun. 11, 2014.
UniProtKB/Swiss-Prot Accession No. P04626.1, Apr. 16, 2014. H.
UniProtKB/Swiss-Prot Accession No. P05121.1, Apr. 16, 2014.
UniProtKB/Swiss-Prot Accession No. P05231.1, Jun. 11, 2014.
UniProtKB/Swiss-Prot Accession No. P09038.3, Jun. 11, 2014.
UniProtKB/Swiss-Prot Accession No. P10145.1, Jun. 11, 2014.
UniProtKB/Swiss-Prot Accession No. P13500.1, Jun. 11, 2014.
UniProtKB/Swiss-Prot Accession No. P14210.2, Jun. 11, 2014.
UniProtKB/Swiss-Prot Accession No. P14780.3, Jun. 11, 2014.
UniProtKB/Swiss-Prot Accession No. P14902.1, May 14, 2014.
UniProtKB/Swiss-Prot Accession No. P15692.2, Jun. 11, 2014.
UniProtKB/Swiss-Prot Accession No. P16035.2, Jun. 11, 2014.
UniProtKB/Swiss-Prot Accession No. P16410.3, Apr. 16, 2014.
UniProtKB/Swiss-Prot Accession No. P48061.1, Jun. 18, 2014.
UniProtKB/Swiss-Prot Accession No. P80162.4, Jun. 11, 2014.
UniProtKB/Swiss-Prot Accession No. P98066.2, Feb. 19, 2014.
UniProtKB/Swiss-Prot Accession No. Q8TD00.3, Mar. 19, 2014.
UniProtKB/Swiss-Prot Accession No. Q96HF1.2, May 14, 2014.
UniProtKB/Swiss-Prot Accession No. Q9BQ51.2, Mar. 19, 2014.
UniProtKB/Swiss-Prot Accession No. Q9HCB6.2, Jun. 11, 2014.
UniProtKB/Swiss-Prot Accession No. Q9NZQ7.1, Apr. 16, 2014.
van der Bruggen et al. "T Cell-Defined Tumor Antigens." *Cancer Immunity.* (2013). Http:www.cancerimmunity.org/peptide.
Venturoni et al. "Investigations into the Polymorphism of Rat Tail Tendon Fibrils Using Atomic Force Microscopy." *Biochem. Biophys. Res. Commun.* 303.2(2003):508-513.
Vincent et al. "Stem Cell Differentiation: Post-Degradation Forces Kick in." *Nat. Mater.* 12.5(2013):384-386.
Vogel et al. "Local Force and Geometry Sensing Regulate Cell Functions." *Nat. Rev. Mol. Cell Biol.* 7.4(2006):265-275.
Wang et al. "Mechanotransduction at a Distance: Mechanically Coupling the Extracellular Matric with the Nucleus." *Nat. Rev. Mol. Cell. Biol.* 10.1(2009):75-82.
Wang-Gillam et al. "A Phase I Study of IMP321 and Gemcitabine as the Front-Line Therapy in Patients with Advanced Pancreatic Adenocarcinoma." *Invest. New Drugs.* 31.3(2013):707-713.
Warner et al. "Cyclooxygenases: New Forms, New Inhibitors, and Lessons from the Clinic." *FASEB J.* 18.7(2004):790-804.
Weisenberger et al. "Comprehensive DNA Methylation Analysis on the Illumina® Infinium® Assay Platform." Illumina, Inc. Mar. 25, 2008. Web.

(56) References Cited

OTHER PUBLICATIONS

Weiss et al. "The Demonstration of Rupture of Cell Surfaces by an Immunological Technique." *Exp. Cell Res.* 30(1963):331-338.
Wen et al. "Mechanically Robust Gelatin-Alginate Ipn Hydrogels by a Combination of Enzymatic and Ionic Crosslinking Approaches." *Macromol. Mater. Eng.* 299(2013):504-513.
Wieland et al. "Engineering Molecular Circuits Using Synthetic Biology in Mammalian Cells." *Annu. Rev. Chem. Biomol. Eng.* 3(2012):209-234.
Wipff et al. "Myofibroblast Contraction Activates Latent TGF-β1 from the Extracellular Matrix." *J. Cell Biol.* 179.6(2007):1311-1323.
Wong et al. "Focal Adhesion Kinase Links Mechanical Force to Skin Fibrosis via Inflammatory Signaling." *Nat. Med.* 18.1(2011):148-152.
Wong et al. "Mechanical Force Prolongs Acute Inflammation via T-Cell-Dependent Pathways During Scar Formation." *FASEB. J.* 25.12(2011):4498-4510.
Wong et al. "Pushing Back: Wound Mechanotransduction in Repair and Regeneration." *J. Invest. Dermatol.* 131.11(2011):2186-2196.
Wozniak et al. "Mechanotransduction in Development: A Growing Role for Contractility." *Nat. Rev. Mol. Cell Biol.* 10.1(2009):34-43.
Yeung et al. "Effects of Substrate Stiffness on Cell Morphology, Cytoskeletal Structure, and Adhesion." *Cell Motil. Cytoskeleton.* 60.1(2005):24-34.
Yoo et al. "Bio-Inspired, Bioengineered and Biomimetic Drug Delivery Carriers." *Nat. Rev. Drug Discov.* 10.7(2011):521-535.
Yoon. "Hidden Markov Models and their Applications in Biological Sequene Analysis." *Curr. Genomics.* 10.6(2009):402-415.
Young et al. "Gelatin as a Delivery Vehicle for the Controlled Release of Bioactive Molecules." *J. Control. Release.* 109.1-3(2005):256-274.
Zemel et al. "Optimal Matrix Rigidity for Stress Fibre Polarization in Stem Cells." *Nat. Phys.* 6.6(2010):468-473.
Zhang et al. "A Tension-Induced Mechanostransduction Pathway Promotes Epithelial Morphogenesis." *Nature.* 471.7336(2011):99-103.
Zhang et al. "Talin Depletion Reveals Independence of Initial Cell Spreading from Integrin Activation and Traction." *Nat. Cell Biol.* 10.9(2008):1062-1068.
Zhao et al. "Stress-Relaxation Behavior in Gels with Ionic and Covalent Crosslinks." *J. Appl. Phys.* 107.6(2010):63509.

\* cited by examiner

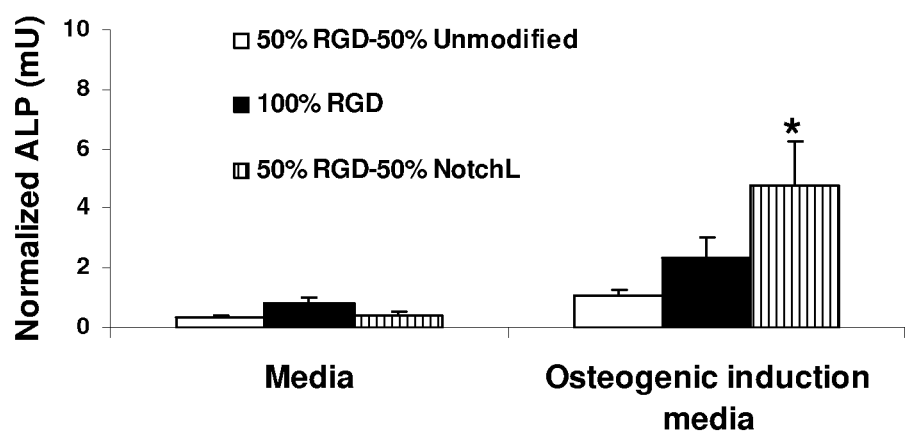

MATERIALS PRESENTING NOTCH SIGNALING MOLECULES TO CONTROL CELL BEHAVIOR

RELATED APPLICATIONS

This application is a national stage application, filed under 35 U.S.C. §371, of International Application No. PCT/US2011/059710, filed Nov. 8, 2011, which claims the benefit of priority under 35 U.S.C. §119(e) to U.S. Provisional Application No. 61/411,129, filed on Nov. 8, 2010, which is incorporated herein by reference in its entirety their entireties.

STATEMENT AS TO FEDERALLY SPONSORED RESEARCH

This invention was made with Government support under NIH DE013349 awarded by the National Institutes of Health. The Government has certain rights in the invention.

FIELD OF THE INVENTION

The invention relates to compositions and methods for delivering cell signaling molecules.

INCORPORATION BY REFERENCE OF SEQUENCE LISTING

The contents of the text file named "29297-081N01US_ST25.txt", which was created on Feb. 12, 2015 and is 24 KB in size, are thereby incorporated by reference in their entirety.

BACKGROUND OF THE INVENTION

A wide variety of mammalian cells use the Notch signaling for embryonic development and maintenance of homeostasis. Notch signaling pathway influences cell fate decisions, such as cell differentiation, survival/apoptosis, and cell cycle in both physiologic and pathologic contexts, particularly in conjunction with stem cell behavior.

SUMMARY OF THE INVENTION

The invention provides a solution to the problem of delivering molecules in a physiologically relevant manner to direct cell fate. For example, a Notch ligand molecule is presented in a microenvironment that mimics the environment encountered in vivo. Accordingly, the invention features a cell delivery vehicle comprising a biocompatible hydrogel or polymer and a composition that binds to a Notch receptor and methods of directing cell fate, e.g., stem cell differentiation, using such compositions. In one example, the composition is covalently linked (e.g., chemically linked) to hydrogel or polymer. A covalent bond is a form of chemical bonding that is characterized by the sharing of pairs of electrons between atoms. Covalent bonds include σ-bonds, π-bonds, metal-to-metal bonds, agostic interactions, and three-center two-electron bonds. Notch receptors include Notch-1, Notch-2, Notch-3, or Notch-4, and compositions that bind to Notch receptors include Delta-like1, Delta-like3, Delta-like4, Jagged1, or Jagged2 or fragments thereof.

Purified populations of cells, e.g., terminally differentiated cells or stem/progenitor cells, are seeded into the cell delivery devices/vehicles and encounter the Notch ligand while the cells are in residence in the vehicle. The stem cells are initially (prior to administration to a subject) located, e.g., encapsulated, inside the vehicle. Following administration to a subject such as a human patient, and residence in the vehicle, the cells migrate out of the vehicle to another site in the body. Exposure to the ligand molecules initiate Notch signaling, which in turn leads to cell proliferation, migration, and/or differentiation of the cells that subsequently leave the delivery vehicle and migrate out to tissues in the body outside of the delivery device/vehicle. The cells comprise stem cells. For example, sources of stem cells include embryonic stem cells, stem cells derived from fetal organ/tissue (e.g., umbilical cord, umbilical cord blood, amniotic fluid), or stem cells derived from adult organ/tissue (e.g., mesenchymal stem cell derived from bone marrow, adipose tissue, blood vessels and etc).

Thus, a method of modulating behavior of a target cell is carried out by transiently contacting the target cell with the vehicle described above. For example, a method of inducing differentiation of a mesenchymal stem cell is carried out by transiently contacting the mesenchymal stem cell with a cell delivery vehicle comprising a biocompatible hydrogel or polymer and a composition that binds to a Notch receptor, wherein the composition comprises human Jagged-1 or a fragment thereof. The cell delivery vehicle promotes differentiation of mesenchymal stem cells into cartilage, bone, or adipose tissues.

The vehicles and methods are useful for regenerative medicine and tissue engineering such as bone regeneration in vivo and ex vivo. To promote differentiation of a cell, e.g., a mesenchymal stem cell, for purposes of bone generation or regeneration, the cell is seeded into or encapsulated into a hydrogel/polymer matrix to which a Notch ligand, an extracellular matrix composition has been conjugated or associated, and exposed to an osteogenic factor such as a bone morphogenic protein. Thus, a method for promoting tissue repair or regeneration is carried out by introducing into a mammal the cell delivery vehicle described above. The vehicle comprises a biocompatible hydrogel or polymer to which a composition that binds to a Notch receptor is linked and a stem cell therein.

The cell delivery vehicle comprises a cell-compatible (physiologically-acceptable) composition such as a gel or polymeric composition. Exemplary compositions include alginates and alginate derivatives, polylactic acid, polyglycolic acid, polylactide-co-glycolide polymers, gelatin, collagen, fibrin, hyaluronic acid, laminin rich gels, agarose, natural and synthetic polysaccharides, polyamino acids, polypeptides, polyesters, polyanhydrides, polyphosphazines, poly(vinyl alcohols), poly(alkylene oxides), poly(allylamines)(PAM), poly(acrylates), modified styrene polymers, pluronic polyols, polyoxamers, poly(uronic acids), poly(vinylpyrrolidone) and copolymers or graft copolymers of any of the above. One preferred scaffold composition includes an RGD-modified alginate.

The Notch ligands or fragments thereof are purified. All proteins or polypeptides to be used in the methods described herein are purified, e.g., isolated from natural sources or chemically synthesized. For example, the Notch ligand is a recombinant gene product such as a soluble fragment of the full-length naturally-occurring sequence. A purified preparation comprises at least 75%, 80%, 90% or 99%-100% proteins or polypeptide by weight (w/w). Stem cells, e.g., bone-marrow derived mesenchymal stem cells, used in the methods are purified or isolated. With regard to cells, the term "isolated" means that the cell is substantially free of other cell types or cellular material with which it naturally occurs. In some cases, a cell population is enriched for a desired cell type such as a stem cell. For example, a sample of cells of a particular tissue type or phenotype is enriched when it is at least 60% of the cell population is of the desired cell/tissue type or phenotype. Preferably, the preparation is at least 75%, more preferably at least 90%, and most preferably at least 99% or 100%, of the cell population. Purity is measured by any appropriate standard method, for example, by fluorescence-activated cell sorting (FACS).

Other features and advantages of the invention will be apparent from the following description of the preferred embodiments thereof, and from the claims. References cited, including the contents of GENBANK Accession Numbers are hereby incorporated by reference.

BRIEF DESCRIPTION OF THE DRAWINGS

FIG. 1 is a bar graph showing stem cell differentiation in response to residence of the cells in biomaterials to which peptide molecules are coupled.

DETAILED DESCRIPTION OF THE INVENTION

The notch signaling pathway is a highly conserved cell signaling system present in most multicellular organisms. Mammals possess four different notch receptors, referred to as Notch1, Notch2, Notch3, and Notch4. The notch receptor is a single-pass transmembrane receptor protein. It is a hetero-oligomer composed of a large extracellular portion, which associates in a calcium-dependent, non-covalent interaction with a smaller piece of the notch protein composed of a short extracellular region, a single transmembrane-pass, and a small intracellular region.

Four Notch receptors (Notch1-Notch4) and five structurally similar Notch ligands (Delta-like1, Delta-like3, Delta-like4, Jagged1, and Jagged2) have been identified in mammals. Because theses ligand proteins are cell membrane bound, direct cell-cell contact is required for the signaling. Thus by providing a synthetic or natural material that can present these Notch ligand protein molecules, or the peptide sequence of the proteins, one can mimic or modulate the signaling, and affect cell fate.

Human Jagged1 is described in U.S. Pat. No. 7,304,138 (e.g., full length protein, SEQ ID NO:1; isolated soluble Jagged1 fragment, SEQ ID NO:2; nucleic acid sequence encoding Jagged1, of U.S. Pat. No. 7,304,138), the disclosure and sequences of which are hereby incorporated by reference). The amino acid sequences and nucleic acid sequences encoding Notch receptors and Notch ligands are available on GENBANK™ using the following accession numbers: human Notch1 protein: CAG33502 (GI: 48146559), incorporated herein by reference; human Notch2 protein: AAB19224 (GI:1679774), incorporated herein by reference; human Notch3 protein: AAB91371 (GI: 2668592), incorporated herein by reference; human Notch4 protein: AAC63097 (GI:1841543), incorporated herein by reference; human Notch1 mRNA: NM_017617 (GI: 148833507), incorporated herein by reference; human Notch2 mRNA: NM_024408 (GI:317008612), incorporated herein by reference; human Notch3 mRNA: NM_000435 (GI:134244284), incorporated herein by reference; human Notch 4 mRNA: NM_004557 (GI:55770875), incorporated herein by reference; Human delta-like 1 protein: EAW47425 (GI:119567810), incorporated herein by reference; Human delta-like 3 protein: AAH00218 (GI:12652923), incorporated herein by reference; Human delta-like 4 protein: EAW92466 (GI:119612872), incorporated herein by reference; Human delta-like 1 mRNA: NM_005618 (GI: 110735442), incorporated herein by reference; Human delta-like 3 mRNA: BC000218 (GI:34783039), incorporated herein by reference; Human delta-like 4 mRNA: NM_019074 (GI:301601642), incorporated herein by reference; Human Jagged1 protein: AAC51731 (GI:2228793), incorporated herein by reference; Human Jagged2 protein: AAD15562 (GI:4314285), incorporated herein by reference; Human Jagged1 mRNA: NM_000214 (GI:168480146), incorporated herein by reference; and Human Jagged2 mRNA: NM_145159 (GI:21704278), incorporated herein by reference (the contents of each accession number listed above is hereby incorporated by reference).

The amino acid sequence of encoding human Jagged1 provided by GenBank Accession No. AAC51323 (GI: 2130537), is incorporated herein by reference, and is shown below (SEQ. ID NO: 1)

```
  1   MRSPRTRGRS  GRPLSLLLAL  LCALRAKVCG  ASGQFELEIL  SMQNVNGELQ
 51   NGNCCGGARN  PGDRKCTRDE  CDTYFKVCLK  EYQSRVTAGG  PCSFGSGSTP
101   VIGGNTFNLK  ASRGNDRNRI  VLPFSFAWPR  SYTLLVEAWD  SSNDTVQPDS
151   IIEKASHSGM  INPSRQWQTL  KQNTGVAHFE  YQIRVTCDDY  YYGFGCNKFC
201   RPRDDFFGHY  ACDQNGNKTC  MEGWMGPECN  RAICRQGCSP  KHGSCKLPGD
251   CRCQYGWQGL  YCDKCIPHPG  CVHGICNEPW  QCLCETNWGG  QLCDKDLNYC
301   GTHQPCLNGG  TCSNTGPDKY  QCSCPEGYSG  PNCEIAEHAC  LSDPCHNRGS
351   CKETSLGFEC  ECSPGWTGPT  CSTNIDDCSP  NNCSHGGTCQ  DLVNGFKCVC
401   PPQWTGKTCQ  LDANECEAKP  CVNAKSCKNL  IASYYCDCLP  GWMGQNCDIN
451   INDCLGQCQN  DASCRDLVNG  YRCICPPGYA  GDHCERDIDE  CASNPCLNGG
501   HCQNEINRFQ  CLCPTGFSGN  LCQLDIDYCE  PNPCQNGAQC  YNRASDYFCK
551   CPEDYEGKNC  SHLKDHCRTT  PCEVIDSCTV  AMASNDTPEG  VRYISSNVCG
601   PHGKCKSQSG  GKFTCDCNKG  FTGTYCHENI  NDCESNPCRN  GGTCIDGVNS
```

```
                           -continued
 651   YKCICSDGWE GAYCETNIND CSQNPCHNGG TCRDLVNDFY CDCKNGW1CGK

701   TCHSRDSQCD EATCNNGGTC YDEGDAFKCM CPGGWEGTTC NIARNSSCLP

751   NPCHNGGTCV VNGESFTCVC KEGWEGPICA QNTNDCSPHP CYNSGTCVDG

801   DNWYRCECAP GFAGPDCRIN INECQSSPCA FGATCVDEIN GYRCVCPPGH

851   SGAKCQEVSG RPCITMGSVI PDGAKWDDDC NTCQCLNGRI ACSICVWCGPR

901   PCLLHKGHSE CPSGQSCIPI LDDQCFVHPC TGVGECRSSS LQPVKTKCTS

951   DSYYQDNCAN ITFTFNKEMM SPGLTTEHIC SELRNLNILK NVSAEYSIYI

1001   ACEPSP SAM EIHVAISAED IRDDGNPIKE ITDKIIDLVS KRDGNSSLIA

1051   AVAEVRVQRR PLKNRTDFLV PLLSSVLTVA WICCLVTAFY WCLRKRRKPG

1101   SHTHSASEDN TTNNVREQLN QIKNPIEKHG ANTVPI1CDYE NKNSKMSKIR

1151   THNSEVEEDD MDKHQQKARF GKQPAYTLVD REEKPPNGTP TKHPNWTNKQ

1201   DNRDLESAQS LNRMEYIV
```

The amino acid sequence of isolated soluble Jagged 1, is incorporated herein by reference, and is shown below (SEQ. ID NO: 2)

```
   1   MRSPRTRGRS RPLSLLLALL CALRAKVCGA SGQFELEILS MQNVNGELQN

51   GNCCGGARNP GDRKCTRDEC DTYFKVCLKE YQSRVTAGGP CSFGSGSTPV

101   TGGNTFNLKA SRGNDRNRIV LPFSFAWPRS YTLLVEAWDS SNDTVQPDSI

151   IEKASHSGMI NPSRQWQTLK QNTGVAHFEY QIRVTCDDYY YGFGCNKFCR

201   PRDDFFGHYA CDQNGNKTCM EGWMGPECNR AICRQGCSPK HGSCKLPGDC

251   RCQYGWQGLY CDKCIPHPGC VHGICNEPWQ CLCETNWGGQ LCDKDLNYCG

301   THQPCLNGGT CSNTGPDKYQ CSCPEGYSGP NCEIAEHACL SDPCHNRGSC

351   KETSLGFECE CSPGWTGPTC STNIDDCSPN NCSHGGTCQD LVNGFKCVCP

401   PQWTGKTCQL DANECEAKPC VNAKSCKNLI ASYYCDCLPG WMGQNCDINI

451   NDCLGQCQND ASCRDLVNGY RCICPPGYAG DHCERDIDEC ASNPCLNGGR

501   CQNEINRFQC LCPTGFSGNL CQLDIDYCEP NPCQNGAQCY NRASDYFCKC

551   PEDYEGKNCS HLKDHCRTTP CEVIDSCTVA MASNDTPEGV RYISSNVCGP

601   HGKCKSQSGG KFTCDCNKGF TGTYCHENIN DCESNPCRNG GTCIDGVNSY

651   CICSDGWEGA YCETNINDCS QNPCHNGGTC RDLVNDFYCD CKNGWKGKTC

701   HSRDSQCDEA TCNNGGTCYD EGDAFKCMCP GGWEGTTCNI ARNSSCLPNP

751   CHNGGTCVVN GESFTCVCKE GWEGPICAQN TNDCSPHPCY NSGTCVDGDN

801   WYRCECAPGF AGPDCRININ ECQSSPCAFG ATCVDEINGY RCVCPPGHSG

851   AKCQEVSGRP CITMGSVIPD GAKWDDDCNT CQCLNGRIAC SKVWCGPRPC

901   LLHKGHSECP SGQSCIPILD DQCFVHPCTG VGECRSSSLQ PVKTKCTSDS

951   YYQDNCANIT FTFNKEMMSP GLTTEHICSE LRNLNILKNV SAEYSIYIAC

1001   EPSPSANNEI HVAISAEDIR DDGNPIKEIT DKIIDLVSKR DGNSSLIAAV

1051   AEVRVQRRPL KNRTD
```

Cell signaling molecules have been coupled onto synthetic or natural materials. For example, protein or peptide molecules specific for cell adhesion receptors, such as Arginine-Glycine-Aspartic Acid (commonly referred as RGD) have been coupled to a variety of materials to enhance their cell adhesion capability, and control cell behavior. These materials recapitulate some key aspects of the cell-ECM interaction by presenting an ECM analog by coupling molecules containing the RGD sequence. Unlike previous methods, the compositions described herein utilize engineered biomaterials, e.g., hydrogels or polymeric compositions, to which Notch ligand molecules are linked. These compositions have been used to successfully modulate cell behavior due to the mimicry effect of cell-cell signaling.

Compositions for Local Presentation of Notch Ligand Molecules in a Cell Carrier

Composition to control the local presentations of these Notch ligand molecules are made by coupling these protein molecules on 3-D polymeric material systems. The spatial and temporal presentation of these molecules are controlled accurately by fine-tuning the chemical reactions used to couple these protein molecules, as well as the physical and chemical properties of the polymer material.

The compositions and methods are especially useful for developing cell delivery vehicles for transplanting terminally differentiated cells or stem/progenitor cells, because the signals resulted from Notch signaling molecules coupled to the polymer system as the cell carrier are accurately controlled to achieve desired cell proliferation, migration, and differentiation.

The cell carrier compositions utilize an injectable or implantable biocompatible polymer material system to which Notch ligand protein or peptide molecules, together with molecules that mediate cell adhesion, are coupled to control differentiated, stem and progenitor cell behavior. Hydrogel and/or polymeric compositions include those described in PCT/US 97/16890 filed Sep. 19, 1997, or U.S. Pat. No. 6,748,954, both of which are hereby incorporated by reference.

Protocol of Coupling Notch Ligand to Alginate

Step 1: Coupling N-β-Maleimidopropionic acid) Hydrazide to Alginate (1.6%)

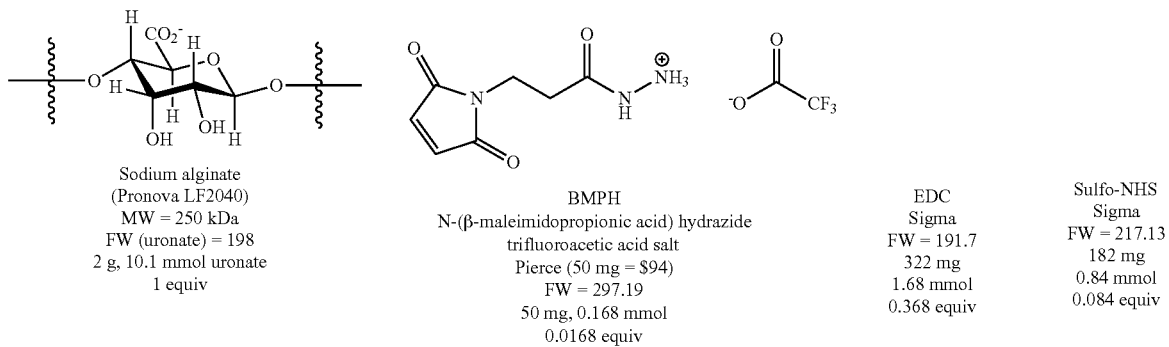

Sodium alginate
(Pronova LF2040)
MW = 250 kDa
FW (uronate) = 198
2 g, 10.1 mmol uronate
1 equiv BMPH
N-(β-maleimidopropionic acid) hydrazide
trifluoroacetic acid salt
Pierce (50 mg = $94)
FW = 297.19
50 mg, 0.168 mmol
0.0168 equiv EDC
Sigma
FW = 191.7
322 mg
1.68 mmol
0.368 equiv Sulfo-NHS
Sigma
FW = 217.13
182 mg
0.84 mmol
0.084 equiv

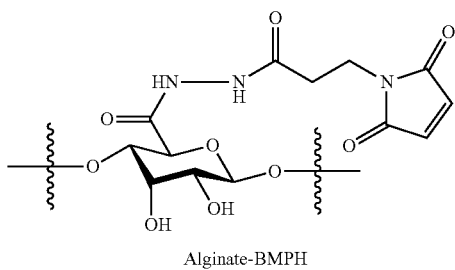

Alginate-BMPH

Protocol A (1.6% Theoretical Coupling≈DS10 for HMW Alginate≈DS10 for LMW Alginate):
1. Prepare 0.1 M MES buffer (dissolve 9.76 g MES in 500 mL double distilled water) and adjust the pH to 6.5 (with concentrated aqueous NaOH solution)
2. Prepare 1% w/w alginate by dissolving 2 g of alginate in 200 mL MES buffer and stirring overnight at room temperature
3. Add 182 mg of NHS followed by 1.68 mg EDC followed by 50 mg of BMPH
4. Allow to stir at room temperature overnight
5. Quench the reaction by the addition of 115 mg hydroxylamine and stir for 30 min
6. Transfer the reaction mixture to dialysis membranes (MWCO 3500, approximately 25 cm per 100 ml of solution)
7. Transfer dialysis membranes to 4 L buckets with dd $H_2O$. Dialyze with decreasing salt concentrations (NaCl per 4 L dd $H_2O$: 30 g-25 g-20 g-15 g-10 g-5 g-0 g-0 g-0 g-0 g)
8. Add a stir bar and change water 3 times per day
9. Transfer the alginate solutions and sterile filter into a sterile autoclaved glass bottle (0.22μ) and dilute to a final volume of 400 mL (==>final concentration of 0.5 mg/mL).
10. Freeze and lyophilize Step 2: Conjugating Notch Ligand Peptide to BMPH-Alginate Protocol:
1. Dissolve 2 mg Notch ligand peptide (AnaSpec Fremont, Calif.) (0.949 μmol) in 2 mL dd $H_2O$
2. Add 50 μL of 0.5 M aqueous TCEP (25 μmol) to 2 mg peptide solution and incubate for 5 minutes at room temperature
3. Mix the activated peptide solution with 10 mL aqueous alginate-BMPH solution (from step 9 of the previous protocol) and stir the mixture overnight at room temperature.
4. Dialyze the resulting mixture against dd water (MWCO 6-8000) against dd water
5. Sterile filter (0.2 micron), freeze and lyophilize

EXAMPLE 1

Notch Ligand Peptide Coupled to Engineered Biomaterials Affects Stem Cell Differentiation Studies were carried out to test the effect of a polymeric alginate biomaterial coupled with peptide molecules (a) derived from one type of Notch ligand molecule, Jagged-1, and (2) peptide molecules containing Arginine-Glycine-Aspartic Acid sequences, on mesenchymal stem cell differentiation in vitro.

A cloned mouse mesenchymal stem cell line was used in the study. Cells encapsulated in the 3-D alginate hydrogels covalently coupled with either only RGD peptide (100%

H-Cys-Asp-Asp-Tyr-Tyr-Tyr-Gly-Phe-Gly-Cys-Asn-Lys-Phe-Cys-Arg-Pro-Arg-OH (SEQ ID NO: 3)

CDDYYYGFGCNKFCRPR
MW = 2107.4
2 mg
0.949 micromol

Tris[2-carboxyethyl] phosphine (TCEP)
0.5M, 0.05 mL, 25 equiv, 0.025 mmol
stir for 5 min at room temp H-Cys-Asp-Asp-Tyr-Tyr-Tyr-Gly-Phe-Gly-Cys-Asn-Lys-Phe-Cys-Arg-Pro-Arg-OH (SEQ ID NO: 3)

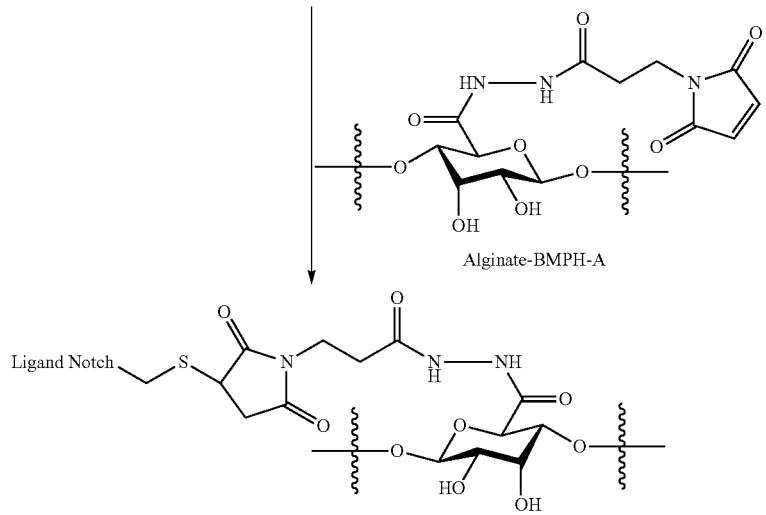

Alginate-BMPH-A

Bondbreaker TCEP solution (5 mL, 0.5 M, Thermo, product #77720)

Slide-A-Lyzer Dialysis Cassette (Pierce Biotech) (MWCO 5000) for dialysis.

RGD), or with covalently coupled Notch ligand peptide molecules (50% RGD-50% NotchL), or mixed with unmodified alginate materials (50% RGD-50% unmodified) were exposed to osteogenic differentiation media or normal media. Osteogenic differentiation media: DMEM (Invitrogen), 10% fetal bovine serum (ATCC, Manassus, Va.), 100 units/ml penicillin and streptomycin, 50 microgram/mL ascorbic acid, 10 mM beta-glycerophosphate, and 0.1 microM dexamethasone. Other examples of osteogenic differentiation media are know in the art, e.g., Nuttelman et al., 2004, Journal of Biomedical Materials Research, 68a (no. 4):773-782; Jaiswal et al., 1997, J. Cell Biochem. 64:295-312, both of which are hereby incorporated by reference). Differentiation media optionally contains a bone morphogenetic protein (BMP), (e.g., BMP-4, Genbank Accession Number: (aa) NP_570912.2 (GI:157276597), (na) NM_001202.3 (GI:157276592), incorporated herein by reference) for osteogenesis. For adipogenic differentiation of mesenchymal stem cells, the media optionally contains angiotensin (GenBank Accession Number 670366A (GI: 229232), incorporated herein by reference) or insulin-like growth factor-I (GenBank Accession Number AAA52789 (GI:184834), incorporated herein by reference).

The amino acid sequence of encoding bone morphogenetic protein 4 provided by GenBank Accession No. NP_570912.2 (GI:157276597), is incorporated herein by reference, and is shown below (SEQ. ID NO: 4)

```
  1 mipgnrmlmv vllcqvllgg ashaslipet gkkkvaeiqg haggrrsgqs hellrdfeat
 61 llqmfglrrr pqpsksavip dymrdlyrlq sgeeeeeqih stgleyperp asrantvrsf
121 hheehlenip gtsensafrf lfnlssipen evissaelrl freqvdqgpd wergfhrini
181 yevmkppaev vpghlitrll dtrlvhhnvt rwetfdvspa vlrwtrekqp nyglaievth
241 lhqtrthqgq hvrisrslpq gsgnwaqlrp llvtfghdgr ghaltrrrra krspkhhsqr
301 arkknkncrr hslyvdfsdv gwndwivapp gyqafychgd cpfpladhln stnhaivqtl
361 vnsvnssipk accvptelsa ismlyldeyd kvvlknyqem vvegcgcr
```

FEATURES Location/Qualifiers
source 1 ... 408
/organism="*Homo sapiens*"
/db_xref="taxon:9606"
/chromosome="14"
/map="14q22-q23"
Protein 1 ... 408
/product="bone morphogenetic protein 4 preproprotein"
/note="bone morphogenetic protein 2B; BMP-4; BMP-2B"
/calculated_mol_wt=44049
sig_peptide 1 ... 24
/inference="COORDINATES: ab initio prediction:SignalP:4.0"
/calculated_mol_wt=2524
Region 36 ... 275
/region_name="TGFb_propeptide"
/note="TGF-beta propeptide; pfam00688"
/db_xref="CDD:250057"
Region 308 ... 408
/region_name="TGFB"
/note="Transforming growth factor-beta (TGF-beta) family; smart00204"
/db_xref="CDD:214556"

The extent of cell differentiation towards osteogenic lineage was assessed by measuring the enzyme production, alkaline phosphatase (ALP). The results indicated that the presence of Notch ligand peptide coupled in alginate polymers promoted stem cell differentiation.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of inducing differentiation of a population of mesenchymal stem cells comprising transiently contacting the population of mesenchymal stem cells with:
   a) a biocompatible alginate hydrogel covalently linked to human Jagged-1, said Jagged-1 comprising the amino acid sequence of SEQ ID NO:1, or a fragment thereof, said fragment comprising the amino acid sequence of SEQ ID NO:2 or SEQ ID NO:3, and
   b) a bone morphogenetic protein,
   thereby inducing differentiation of the population of mesenchymal stem cells into a population of cells of osteogenic lineage, wherein the level of alkaline phosphatase activity of the population of cells after said contacting is increased by at least 4-fold as compared to the level of alkaline phosphatase activity of a population of mesenchymal stem cells that has been contacted with the bone morphogenetic protein but not the alginate hydrogel.

2. The method of claim 1, wherein said bone morphogenetic protein is bone morphogenetic protein-4.

3. The method of claim 1, wherein said population of cells of osteogenic lineage comprises bone cells or cartilage cells.

4. The method of claim 2, wherein said bone morphogenetic protein-4 comprises amino acids 36-275 or 308-408 of SEQ ID NO:4.

5. The method of claim 1, wherein said alginate hydrogel comprises alginate covalently linked to a peptide molecule comprising an arginine-glycine-aspartic acid (RGD) sequence.

* * * * *

SEQUENCE LISTING

<160> NUMBER OF SEQ ID NOS: 4

<210> SEQ ID NO 1
<211> LENGTH: 1218
<212> TYPE: PRT

```
<213> ORGANISM: Homo sapiens

<400> SEQUENCE: 1

Met Arg Ser Pro Arg Thr Gly Arg Ser Gly Arg Pro Leu Ser Leu
 1               5                  10                  15

Leu Leu Ala Leu Leu Cys Ala Leu Arg Ala Lys Val Cys Gly Ala Ser
             20                  25                  30

Gly Gln Phe Glu Leu Glu Ile Leu Ser Met Gln Asn Val Asn Gly Glu
             35                  40                  45

Leu Gln Asn Gly Asn Cys Cys Gly Ala Arg Asn Pro Gly Asp Arg
     50                  55                  60

Lys Cys Thr Arg Asp Glu Cys Asp Thr Tyr Phe Lys Val Cys Leu Lys
 65                  70                  75                  80

Glu Tyr Gln Ser Arg Val Thr Ala Gly Gly Pro Cys Ser Phe Gly Ser
                 85                  90                  95

Gly Ser Thr Pro Val Ile Gly Gly Asn Thr Phe Asn Leu Lys Ala Ser
             100                 105                 110

Arg Gly Asn Asp Arg Asn Arg Ile Val Leu Pro Phe Ser Phe Ala Trp
             115                 120                 125

Pro Arg Ser Tyr Thr Leu Leu Val Glu Ala Trp Asp Ser Ser Asn Asp
 130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                 165                 170                 175

Ala His Phe Glu Tyr Gln Ile Arg Val Thr Cys Asp Asp Tyr Tyr Tyr
             180                 185                 190

Gly Phe Gly Cys Asn Lys Phe Cys Arg Pro Arg Asp Asp Phe Phe Gly
             195                 200                 205

His Tyr Ala Cys Asp Gln Asn Gly Asn Lys Thr Cys Met Glu Gly Trp
             210                 215                 220

Met Gly Pro Glu Cys Asn Arg Ala Ile Cys Arg Gln Gly Cys Ser Pro
225                 230                 235                 240

Lys His Gly Ser Cys Lys Leu Pro Gly Asp Cys Arg Cys Gln Tyr Gly
                 245                 250                 255

Trp Gln Gly Leu Tyr Cys Asp Lys Cys Ile Pro His Pro Gly Cys Val
             260                 265                 270

His Gly Ile Cys Asn Glu Pro Trp Gln Cys Leu Cys Glu Thr Asn Trp
             275                 280                 285

Gly Gly Gln Leu Cys Asp Lys Asp Leu Asn Tyr Cys Gly Thr His Gln
             290                 295                 300

Pro Cys Leu Asn Gly Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                 325                 330                 335

Glu His Ala Cys Leu Ser Asp Pro His Asn Arg Gly Ser Cys Lys
             340                 345                 350

Glu Thr Ser Leu Gly Phe Glu Cys Glu Cys Ser Pro Gly Trp Thr Gly
             355                 360                 365

Pro Thr Cys Ser Thr Asn Ile Asp Asp Cys Ser Pro Asn Asn Cys Ser
 370                 375                 380

His Gly Gly Thr Cys Gln Asp Leu Val Asn Gly Phe Lys Cys Val Cys
385                 390                 395                 400
```

```
Pro Pro Gln Trp Thr Gly Lys Thr Cys Gln Leu Asp Ala Asn Glu Cys
            405                 410                 415
Glu Ala Lys Pro Cys Val Asn Ala Lys Ser Cys Lys Asn Leu Ile Ala
            420                 425                 430
Ser Tyr Tyr Cys Asp Cys Leu Pro Gly Trp Met Gly Gln Asn Cys Asp
            435                 440                 445
Ile Asn Ile Asn Asp Cys Leu Gly Gln Cys Gln Asn Asp Ala Ser Cys
450                 455                 460
Arg Asp Leu Val Asn Gly Tyr Arg Cys Ile Cys Pro Pro Gly Tyr Ala
465                 470                 475                 480
Gly Asp His Cys Glu Arg Asp Ile Asp Glu Cys Ala Ser Asn Pro Cys
            485                 490                 495
Leu Asn Gly Gly His Cys Gln Asn Glu Ile Asn Arg Phe Gln Cys Leu
            500                 505                 510
Cys Pro Thr Gly Phe Ser Gly Asn Leu Cys Gln Leu Asp Ile Asp Tyr
            515                 520                 525
Cys Glu Pro Asn Pro Cys Gln Asn Gly Ala Gln Cys Tyr Asn Arg Ala
            530                 535                 540
Ser Asp Tyr Phe Cys Lys Cys Pro Glu Asp Tyr Glu Gly Lys Asn Cys
545                 550                 555                 560
Ser His Leu Lys Asp His Cys Arg Thr Thr Pro Cys Glu Val Ile Asp
            565                 570                 575
Ser Cys Thr Val Ala Met Ala Ser Asn Asp Thr Pro Glu Gly Val Arg
            580                 585                 590
Tyr Ile Ser Ser Asn Val Cys Gly Pro His Gly Lys Cys Lys Ser Gln
            595                 600                 605
Ser Gly Gly Lys Phe Thr Cys Asp Cys Asn Lys Gly Phe Thr Gly Thr
            610                 615                 620
Tyr Cys His Glu Asn Ile Asn Asp Cys Glu Ser Asn Pro Cys Arg Asn
625                 630                 635                 640
Gly Gly Thr Cys Ile Asp Gly Val Asn Ser Tyr Lys Cys Ile Cys Ser
            645                 650                 655
Asp Gly Trp Glu Gly Ala Tyr Cys Glu Thr Asn Ile Asn Asp Cys Ser
            660                 665                 670
Gln Asn Pro Cys His Asn Gly Gly Thr Cys Arg Asp Leu Val Asn Asp
            675                 680                 685
Phe Tyr Cys Asp Cys Lys Asn Gly Trp Cys Gly Lys Thr Cys His Ser
            690                 695                 700
Arg Asp Ser Gln Cys Asp Glu Ala Thr Cys Asn Asn Gly Gly Thr Cys
705                 710                 715                 720
Tyr Asp Glu Gly Asp Ala Phe Lys Cys Met Cys Pro Gly Gly Trp Glu
            725                 730                 735
Gly Thr Thr Cys Asn Ile Ala Arg Asn Ser Ser Cys Leu Pro Asn Pro
            740                 745                 750
Cys His Asn Gly Gly Thr Cys Val Val Asn Gly Glu Ser Phe Thr Cys
            755                 760                 765
Val Cys Lys Glu Gly Trp Glu Gly Pro Ile Cys Ala Gln Asn Thr Asn
            770                 775                 780
Asp Cys Ser Pro His Pro Cys Tyr Asn Ser Gly Thr Cys Val Asp Gly
785                 790                 795                 800
Asp Asn Trp Tyr Arg Cys Glu Cys Ala Pro Gly Phe Ala Gly Pro Asp
            805                 810                 815
Cys Arg Ile Asn Ile Asn Glu Cys Gln Ser Ser Pro Cys Ala Phe Gly
```

```
                820             825             830
Ala Thr Cys Val Asp Glu Ile Asn Gly Tyr Arg Cys Val Cys Pro Pro
                835             840             845
Gly His Ser Gly Ala Lys Cys Gln Glu Val Ser Gly Arg Pro Cys Ile
                850             855             860
Thr Met Gly Ser Val Ile Pro Asp Gly Ala Lys Trp Asp Asp Cys
865             870             875                         880
Asn Thr Cys Gln Cys Leu Asn Gly Arg Ile Ala Cys Ser Ile Cys Val
                    885             890             895
Trp Cys Gly Pro Arg Pro Cys Leu Leu His Lys Gly His Ser Glu Cys
                900             905             910
Pro Ser Gly Gln Ser Cys Ile Pro Ile Leu Asp Asp Gln Cys Phe Val
                915             920             925
His Pro Cys Thr Gly Val Gly Glu Cys Arg Ser Ser Leu Gln Pro
                930             935             940
Val Lys Thr Lys Cys Thr Ser Asp Ser Tyr Tyr Gln Asp Asn Cys Ala
945             950             955                         960
Asn Ile Thr Phe Thr Phe Asn Lys Glu Met Met Ser Pro Gly Leu Thr
                965             970             975
Thr Glu His Ile Cys Ser Glu Leu Arg Asn Leu Asn Ile Leu Lys Asn
                980             985             990
Val Ser Ala Glu Tyr Ser Ile Tyr  Ile Ala Cys Glu Pro  Ser Pro Ser
                995                 1000             1005
Ala Met  Glu Ile His Val Ala  Ile Ser Ala Glu Asp  Ile Arg Asp
    1010                 1015             1020
Asp Gly  Asn Pro Ile Lys Glu  Ile Thr Asp Lys Ile  Ile Asp Leu
    1025                 1030             1035
Val Ser  Lys Arg Asp Gly Asn  Ser Ser Leu Ile Ala  Ala Val Ala
    1040                 1045             1050
Glu Val  Arg Val Gln Arg Arg  Pro Leu Lys Asn Arg  Thr Asp Phe
    1055                 1060             1065
Leu Val  Pro Leu Leu Ser Ser  Val Leu Thr Val Ala  Trp Ile Cys
    1070                 1075             1080
Cys Leu  Val Thr Ala Phe Tyr  Trp Cys Leu Arg Lys  Arg Arg Lys
    1085                 1090             1095
Pro Gly  Ser His Thr His Ser  Ala Ser Glu Asp Asn  Thr Thr Asn
    1100                 1105             1110
Asn Val  Arg Glu Gln Leu Asn  Gln Ile Lys Asn Pro  Ile Glu Lys
    1115                 1120             1125
His Gly  Ala Asn Thr Val Pro  Ile Cys Asp Tyr Glu  Asn Lys Asn
    1130                 1135             1140
Ser Lys  Met Ser Lys Ile Arg  Thr His Asn Ser Glu  Val Glu Glu
    1145                 1150             1155
Asp Asp  Met Asp Lys His Gln  Gln Lys Ala Arg Phe  Gly Lys Gln
    1160                 1165             1170
Pro Ala  Tyr Thr Leu Val Asp  Arg Glu Glu Lys Pro  Pro Asn Gly
    1175                 1180             1185
Thr Pro  Thr Lys His Pro Asn  Trp Thr Asn Lys Gln  Asp Asn Arg
    1190                 1195             1200
Asp Leu  Glu Ser Ala Gln Ser  Leu Asn Arg Met Glu  Tyr Ile Val
    1205                 1210             1215

<210> SEQ ID NO 2
```

<211> LENGTH: 1065
<212> TYPE: PRT
<213> ORGANISM: Homo sapiens

<400> SEQUENCE: 2

```
Met Arg Ser Pro Arg Thr Arg Gly Arg Ser Arg Pro Leu Ser Leu Leu
1               5                   10                  15

Leu Ala Leu Leu Cys Ala Leu Arg Ala Lys Val Cys Gly Ala Ser Gly
            20                  25                  30

Gln Phe Glu Leu Glu Ile Leu Ser Met Gln Asn Val Asn Gly Glu Leu
        35                  40                  45

Gln Asn Gly Asn Cys Cys Gly Gly Ala Arg Asn Pro Gly Asp Arg Lys
    50                  55                  60

Cys Thr Arg Asp Glu Cys Asp Thr Tyr Phe Lys Val Cys Leu Lys Glu
65                  70                  75                  80

Tyr Gln Ser Arg Val Thr Ala Gly Gly Pro Cys Ser Phe Gly Ser Gly
                85                  90                  95

Ser Thr Pro Val Thr Gly Gly Asn Thr Phe Asn Leu Lys Ala Ser Arg
            100                 105                 110

Gly Asn Asp Arg Asn Arg Ile Val Leu Pro Phe Ser Phe Ala Trp Pro
        115                 120                 125

Arg Ser Tyr Thr Leu Leu Val Glu Ala Trp Asp Ser Ser Asn Asp Thr
    130                 135                 140

Val Gln Pro Asp Ser Ile Ile Glu Lys Ala Ser His Ser Gly Met Ile
145                 150                 155                 160

Asn Pro Ser Arg Gln Trp Gln Thr Leu Lys Gln Asn Thr Gly Val Ala
                165                 170                 175

His Phe Glu Tyr Gln Ile Arg Val Thr Cys Asp Asp Tyr Tyr Tyr Gly
            180                 185                 190

Phe Gly Cys Asn Lys Phe Cys Arg Pro Arg Asp Asp Phe Phe Gly His
        195                 200                 205

Tyr Ala Cys Asp Gln Asn Gly Asn Lys Thr Cys Met Glu Gly Trp Met
    210                 215                 220

Gly Pro Glu Cys Asn Arg Ala Ile Cys Arg Gln Gly Cys Ser Pro Lys
225                 230                 235                 240

His Gly Ser Cys Lys Leu Pro Gly Asp Cys Arg Cys Gln Tyr Gly Trp
                245                 250                 255

Gln Gly Leu Tyr Cys Asp Lys Cys Ile Pro His Pro Gly Cys Val His
            260                 265                 270

Gly Ile Cys Asn Glu Pro Trp Gln Cys Leu Cys Glu Thr Asn Trp Gly
        275                 280                 285

Gly Gln Leu Cys Asp Lys Asp Leu Asn Tyr Cys Gly Thr His Gln Pro
    290                 295                 300

Cys Leu Asn Gly Gly Thr Cys Ser Asn Thr Gly Pro Asp Lys Tyr Gln
305                 310                 315                 320

Cys Ser Cys Pro Glu Gly Tyr Ser Gly Pro Asn Cys Glu Ile Ala Glu
                325                 330                 335

His Ala Cys Leu Ser Asp Pro Cys His Asn Arg Gly Ser Cys Lys Glu
            340                 345                 350

Thr Ser Leu Gly Phe Glu Cys Glu Cys Ser Pro Gly Trp Thr Gly Pro
        355                 360                 365

Thr Cys Ser Thr Asn Ile Asp Asp Cys Ser Pro Asn Asn Cys Ser His
    370                 375                 380

Gly Gly Thr Cys Gln Asp Leu Val Asn Gly Phe Lys Cys Val Cys Pro
```

-continued

```
385                 390                 395                 400

Pro Gln Trp Thr Gly Lys Thr Cys Gln Leu Asp Ala Asn Glu Cys Glu
                405                 410                 415

Ala Lys Pro Cys Val Asn Ala Lys Ser Cys Lys Asn Leu Ile Ala Ser
                420                 425                 430

Tyr Tyr Cys Asp Cys Leu Pro Gly Trp Met Gly Gln Asn Cys Asp Ile
                435                 440                 445

Asn Ile Asn Asp Cys Leu Gly Gln Cys Gln Asn Asp Ala Ser Cys Arg
            450                 455                 460

Asp Leu Val Asn Gly Tyr Arg Cys Ile Cys Pro Pro Gly Tyr Ala Gly
465                 470                 475                 480

Asp His Cys Glu Arg Asp Ile Asp Glu Cys Ala Ser Asn Pro Cys Leu
                485                 490                 495

Asn Gly Gly Arg Cys Gln Asn Glu Ile Asn Arg Phe Gln Cys Leu Cys
                500                 505                 510

Pro Thr Gly Phe Ser Gly Asn Leu Cys Gln Leu Asp Ile Asp Tyr Cys
                515                 520                 525

Glu Pro Asn Pro Cys Gln Asn Gly Ala Gln Cys Tyr Asn Arg Ala Ser
                530                 535                 540

Asp Tyr Phe Cys Lys Cys Pro Glu Asp Tyr Glu Gly Lys Asn Cys Ser
545                 550                 555                 560

His Leu Lys Asp His Cys Arg Thr Thr Pro Cys Glu Val Ile Asp Ser
                565                 570                 575

Cys Thr Val Ala Met Ala Ser Asn Asp Thr Pro Glu Gly Val Arg Tyr
                580                 585                 590

Ile Ser Ser Asn Val Cys Gly Pro His Gly Lys Cys Lys Ser Gln Ser
                595                 600                 605

Gly Gly Lys Phe Thr Cys Asp Cys Asn Lys Gly Phe Thr Gly Thr Tyr
                610                 615                 620

Cys His Glu Asn Ile Asn Asp Cys Glu Ser Asn Pro Cys Arg Asn Gly
625                 630                 635                 640

Gly Thr Cys Ile Asp Gly Val Asn Ser Tyr Cys Ile Cys Ser Asp Gly
                645                 650                 655

Trp Glu Gly Ala Tyr Cys Glu Thr Asn Ile Asn Asp Cys Ser Gln Asn
                660                 665                 670

Pro Cys His Asn Gly Gly Thr Cys Arg Asp Leu Val Asn Asp Phe Tyr
                675                 680                 685

Cys Asp Cys Lys Asn Gly Trp Lys Gly Lys Thr Cys His Ser Arg Asp
                690                 695                 700

Ser Gln Cys Asp Glu Ala Thr Cys Asn Asn Gly Gly Thr Cys Tyr Asp
705                 710                 715                 720

Glu Gly Asp Ala Phe Lys Cys Met Cys Pro Gly Gly Trp Glu Gly Thr
                725                 730                 735

Thr Cys Asn Ile Ala Arg Asn Ser Ser Cys Leu Pro Asn Pro Cys His
                740                 745                 750

Asn Gly Gly Thr Cys Val Val Asn Gly Glu Ser Phe Thr Cys Val Cys
                755                 760                 765

Lys Glu Gly Trp Glu Gly Pro Ile Cys Ala Gln Asn Thr Asn Asp Cys
                770                 775                 780

Ser Pro His Pro Cys Tyr Asn Ser Gly Thr Cys Val Asp Gly Asp Asn
785                 790                 795                 800

Trp Tyr Arg Cys Glu Cys Ala Pro Gly Phe Ala Gly Pro Asp Cys Arg
                805                 810                 815
```

```
Ile Asn Ile Asn Glu Cys Gln Ser Ser Pro Cys Ala Phe Gly Ala Thr
            820                 825                 830

Cys Val Asp Glu Ile Asn Gly Tyr Arg Cys Val Cys Pro Gly His
        835                 840                 845

Ser Gly Ala Lys Cys Gln Glu Val Ser Gly Arg Pro Cys Ile Thr Met
850                 855                 860

Gly Ser Val Ile Pro Asp Gly Ala Lys Trp Asp Asp Cys Asn Thr
865                 870                 875                 880

Cys Gln Cys Leu Asn Gly Arg Ile Ala Cys Ser Lys Val Trp Cys Gly
                885                 890                 895

Pro Arg Pro Cys Leu Leu His Lys Gly His Ser Glu Cys Pro Ser Gly
        900                 905                 910

Gln Ser Cys Ile Pro Ile Leu Asp Asp Gln Cys Phe Val His Pro Cys
        915                 920                 925

Thr Gly Val Gly Glu Cys Arg Ser Ser Leu Gln Pro Val Lys Thr
    930                 935                 940

Lys Cys Thr Ser Asp Ser Tyr Tyr Gln Asp Asn Cys Ala Asn Ile Thr
945                 950                 955                 960

Phe Thr Phe Asn Lys Glu Met Met Ser Pro Gly Leu Thr Thr Glu His
                965                 970                 975

Ile Cys Ser Glu Leu Arg Asn Leu Asn Ile Leu Lys Asn Val Ser Ala
                980                 985                 990

Glu Tyr Ser Ile Tyr Ile Ala Cys  Glu Pro Ser Pro Ser  Ala Asn Asn
                995                1000                1005

Glu Ile  His Val Ala Ile Ser  Ala Glu Asp Ile Arg  Asp Asp Gly
    1010                1015                1020

Asn Pro  Ile Lys Glu Ile Thr  Asp Lys Ile Ile Asp  Leu Val Ser
    1025                1030                1035

Lys Arg  Asp Gly Asn Ser Ser  Leu Ile Ala Ala Val  Ala Glu Val
    1040                1045                1050

Arg Val  Gln Arg Arg Pro Leu  Lys Asn Arg Thr  Asp
    1055                1060                1065

<210> SEQ ID NO 3
<211> LENGTH: 17
<212> TYPE: PRT
<213> ORGANISM: Homo sapiens

<400> SEQUENCE: 3

Cys Asp Asp Tyr Tyr Tyr Gly Phe Gly Cys Asn Lys Phe Cys Arg Pro
1               5                   10                  15

Arg

<210> SEQ ID NO 4
<211> LENGTH: 408
<212> TYPE: PRT
<213> ORGANISM: Homo sapiens

<400> SEQUENCE: 4

Met Ile Pro Gly Asn Arg Met Leu Met Val Val Leu Leu Cys Gln Val
1               5                   10                  15

Leu Leu Gly Gly Ala Ser His Ala Ser Leu Ile Pro Glu Thr Gly Lys
                20                  25                  30

Lys Lys Val Ala Glu Ile Gln Gly His Ala Gly Gly Arg Arg Ser Gly
            35                  40                  45
```

```
Gln Ser His Glu Leu Leu Arg Asp Phe Glu Ala Thr Leu Leu Gln Met
     50                  55                  60

Phe Gly Leu Arg Arg Arg Pro Gln Pro Ser Lys Ser Ala Val Ile Pro
 65                  70                  75                  80

Asp Tyr Met Arg Asp Leu Tyr Arg Leu Gln Ser Gly Glu Glu Glu Glu
                 85                  90                  95

Glu Gln Ile His Ser Thr Gly Leu Glu Tyr Pro Glu Arg Pro Ala Ser
            100                 105                 110

Arg Ala Asn Thr Val Arg Ser Phe His His Glu Glu His Leu Glu Asn
            115                 120                 125

Ile Pro Gly Thr Ser Glu Asn Ser Ala Phe Arg Phe Leu Phe Asn Leu
130                 135                 140

Ser Ser Ile Pro Glu Asn Glu Val Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
                180                 185                 190

Gly His Leu Ile Thr Arg Leu Leu Asp Thr Arg Leu Val His His Asn
            195                 200                 205

Val Thr Arg Trp Glu Thr Phe Asp Val Ser Pro Ala Val Leu Arg Trp
210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
                260                 265                 270

Val Thr Phe Gly His Asp Gly Arg Gly His Ala Leu Thr Arg Arg Arg
            275                 280                 285

Arg Ala Lys Arg Ser Pro Lys His His Ser Arg Ala Arg Lys Lys
290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
            340                 345                 350

Asn His Ala Ile Val Gln Thr Leu Val Asn Ser Val Asn Ser Ser Ile
            355                 360                 365

Pro Lys Ala Cys Cys Val Pro Thr Glu Leu Ser Ala Ile Ser Met Leu
370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
                405
```